United States Patent
Shimizu et al.

(10) Patent No.: US 10,428,003 B2
(45) Date of Patent: Oct. 1, 2019

(54) METHOD FOR PRODUCING ACETIC ACID

(71) Applicant: DAICEL CORPORATION, Osaka-shi, Osaka (JP)

(72) Inventors: Masahiko Shimizu, Himeji (JP); Susumu Goda, Himeji (JP); Hiroyuki Miura, Himeji (JP)

(73) Assignee: DAICEL CORPORATION, Osaka-Shi, Osaka (JP)

( * ) Notice: Subject to any disclaimer, the term of this patent is extended or adjusted under 35 U.S.C. 154(b) by 0 days.

(21) Appl. No.: 15/540,172

(22) PCT Filed: May 25, 2017

(86) PCT No.: PCT/JP2017/019573
§ 371 (c)(1),
(2) Date: Jun. 27, 2017

(87) PCT Pub. No.: WO2018/135014
PCT Pub. Date: Jul. 26, 2018

(65) Prior Publication Data
US 2018/0201562 A1 Jul. 19, 2018

(30) Foreign Application Priority Data

Jan. 18, 2017 (JP) ................. 2017-006645
Mar. 2, 2017 (JP) ................. 2017-039389

(51) Int. Cl.
| | |
|---|---|
| *C07C 51/12* | (2006.01) |
| *C07C 51/44* | (2006.01) |
| *B01D 3/00* | (2006.01) |
| *B01D 3/14* | (2006.01) |
| *B01D 15/36* | (2006.01) |
| *C07C 45/80* | (2006.01) |

(52) U.S. Cl.
CPC .............. *C07C 51/12* (2013.01); *B01D 3/007* (2013.01); *B01D 3/009* (2013.01); *B01D 3/143* (2013.01); *B01D 15/361* (2013.01); *C07C 45/80* (2013.01); *C07C 51/445* (2013.01); *Y02P 20/127* (2015.11)

(58) Field of Classification Search
None
See application file for complete search history.

(56) References Cited

U.S. PATENT DOCUMENTS

| | | | |
|---|---|---|---|
| 5,625,095 | A | 4/1997 | Miura et al. |
| 6,143,930 | A | 11/2000 | Singh et al. |
| 2011/0009665 | A1 | 1/2011 | Scates |
| 2013/0303800 | A1 | 11/2013 | Shimizu |
| 2015/0299084 | A1 | 10/2015 | Shimizu et al. |

FOREIGN PATENT DOCUMENTS

| | | |
|---|---|---|
| EP | 0 687 662 A2 | 12/1995 |
| EP | 2 629 720 A1 | 8/2013 |
| EP | 2 937 329 A1 | 10/2015 |
| JP | 8-67650 A | 3/1996 |
| JP | 2001-508405 A | 6/2001 |
| JP | 2012-532867 A | 12/2012 |
| WO | WO 98/17619 A2 | 4/1998 |
| WO | WO 2011/005304 A2 | 1/2011 |
| WO | WO 2012/046593 A1 | 4/2012 |
| WO | WO 2014/097867 A1 | 6/2014 |

OTHER PUBLICATIONS

English translation of the Written Opinion of the International Searching Authority dated Sep. 1, 2017, in PCT International Application No. PCT/JP2017/019573.
International Search Report dated Aug. 8, 2017, in PCT International Application No. PCT/JP2017/019573.
Written Opinion dated Aug. 8, 2017, in PCT International Application No. PCT/JP2017/019573.
Extended European Search Report dated Jan. 15, 2018, in European Patent Application No. 17731797.1.
Japanese Notification of Reasons for Rejection for Application No. 2017-533362, dated Jul. 3, 2018, with English language translation.

*Primary Examiner* — Ana Z Muresan
(74) *Attorney, Agent, or Firm* — Birch, Stewart, Kolasch & Birch, LLP

(57) ABSTRACT

It is intended to provide an acetic acid production method capable of industrially advantageously separating and removing a by-product acetaldehyde in the separation step of separating a process stream into aqueous and organic phases. In the present invention, the separation step satisfies, for example, the following conditions (vi) to (viii), and at least a portion of the aqueous phase is treated in the acetaldehyde separation and removal step: (vi) acetaldehyde concentrations in the aqueous and/or organic phases are not more than 28.1 mass % and not more than 24.8 mass %, respectively; (vii) a separation temperature is not more than 70° C.; and (viii) methyl acetate concentrations in the aqueous and/or organic phases are not more than 12.0 mass % and not more than 47.6 mass %, respectively, and/or the sum of the methyl acetate concentrations in the aqueous and organic phases is not more than 59.6 mass %.

20 Claims, 6 Drawing Sheets

[Figure 1]
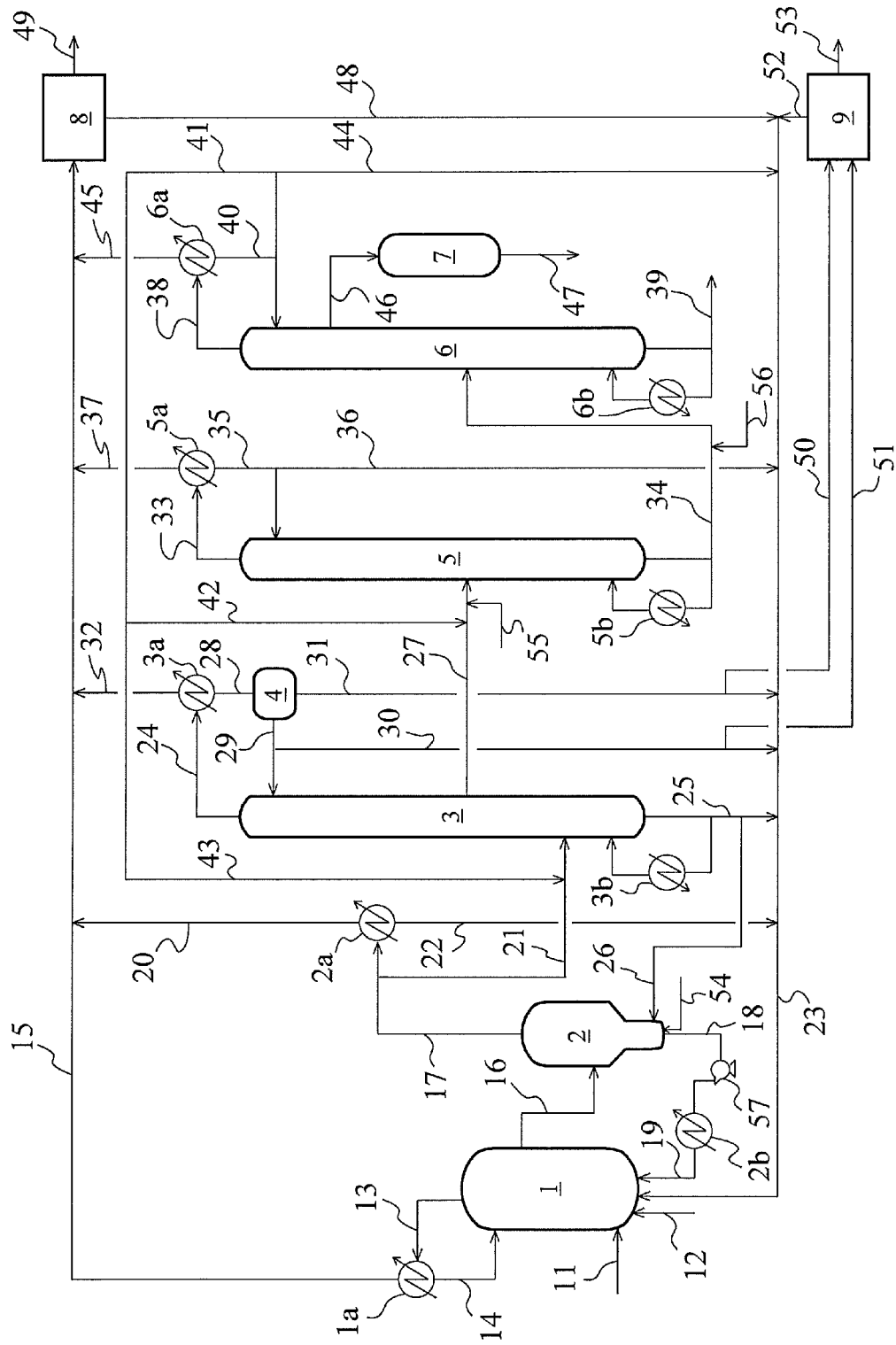

[Figure 2]
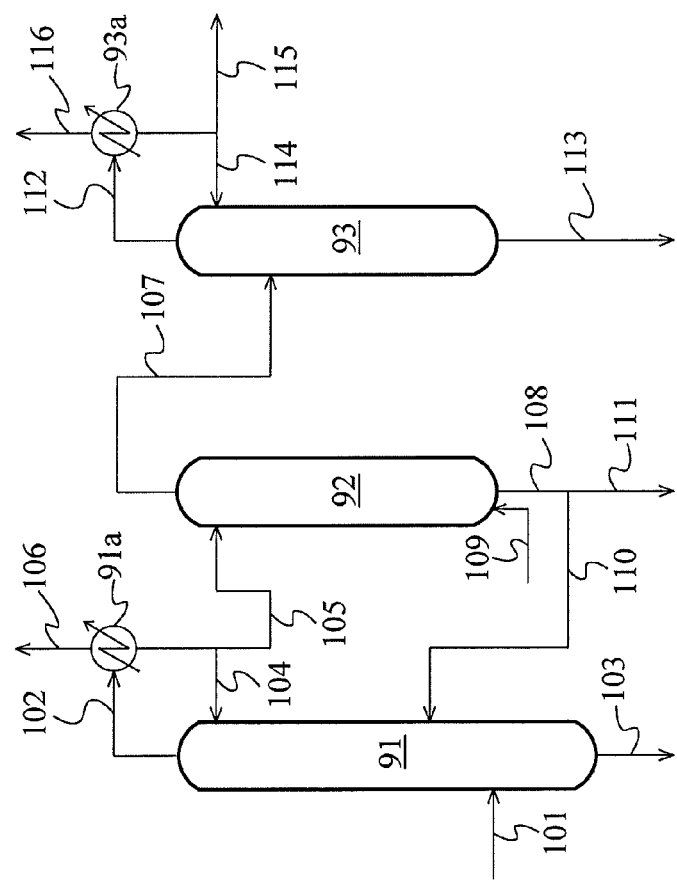

[Figure 3]
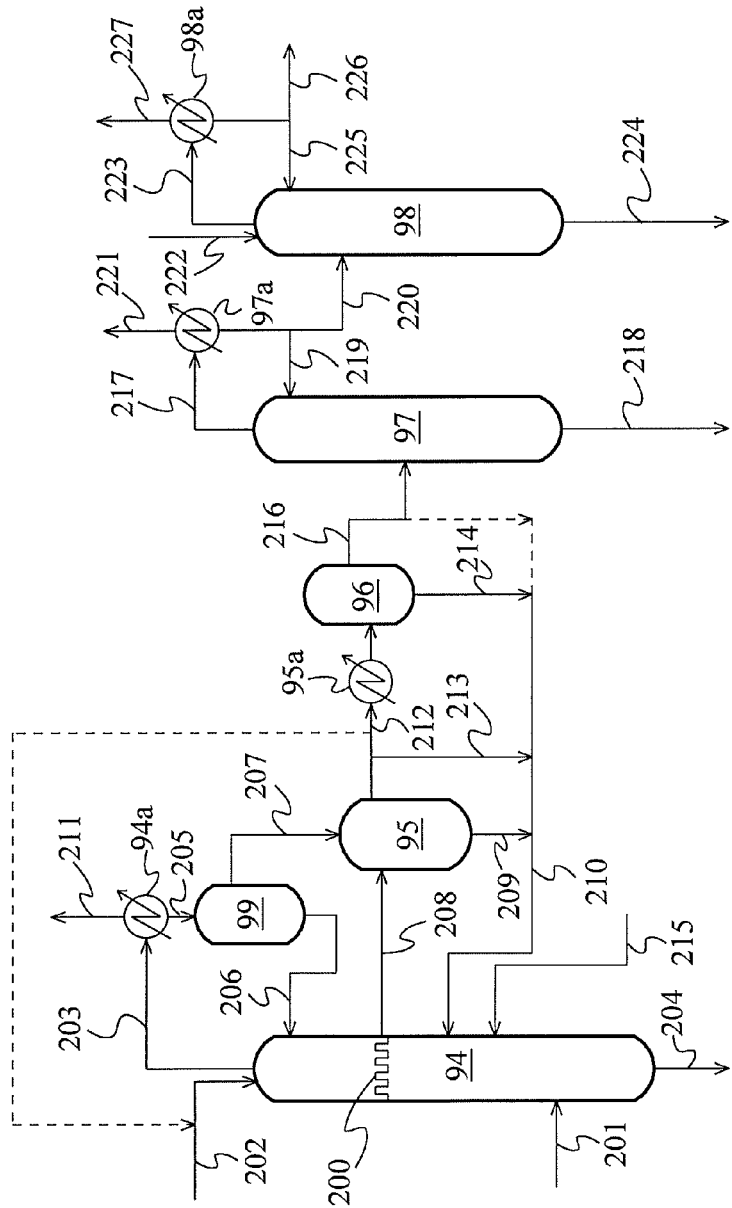

[Figure 4]
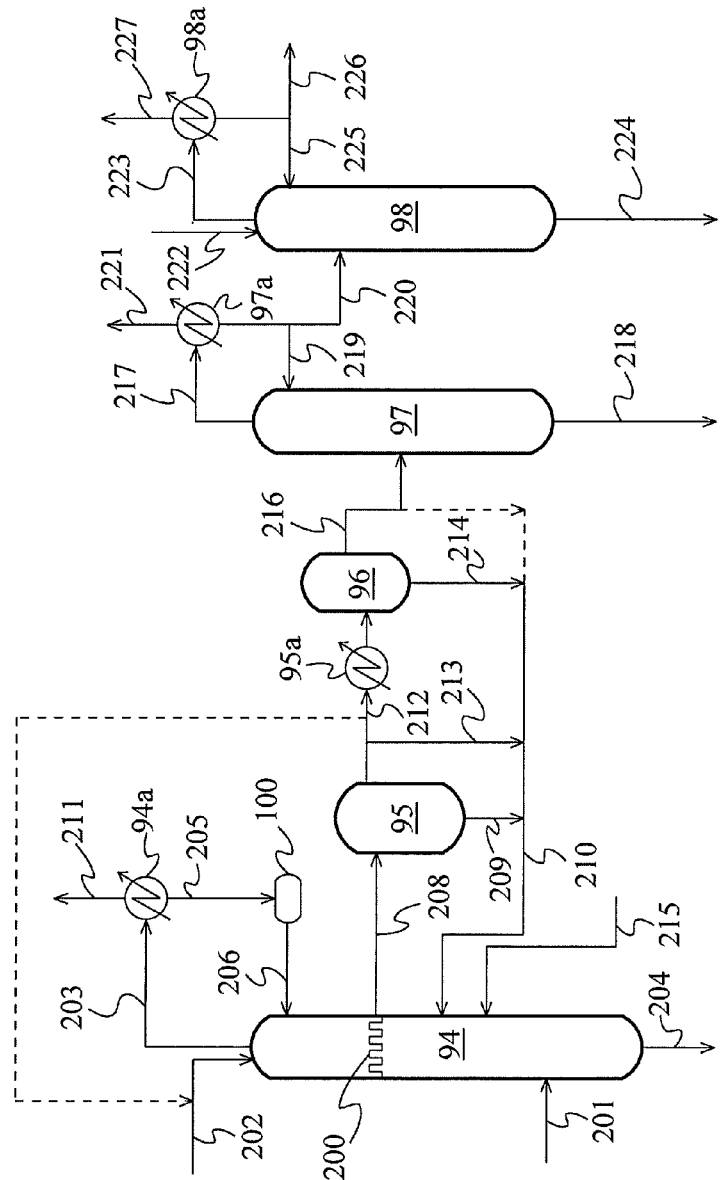

[Figure 5]
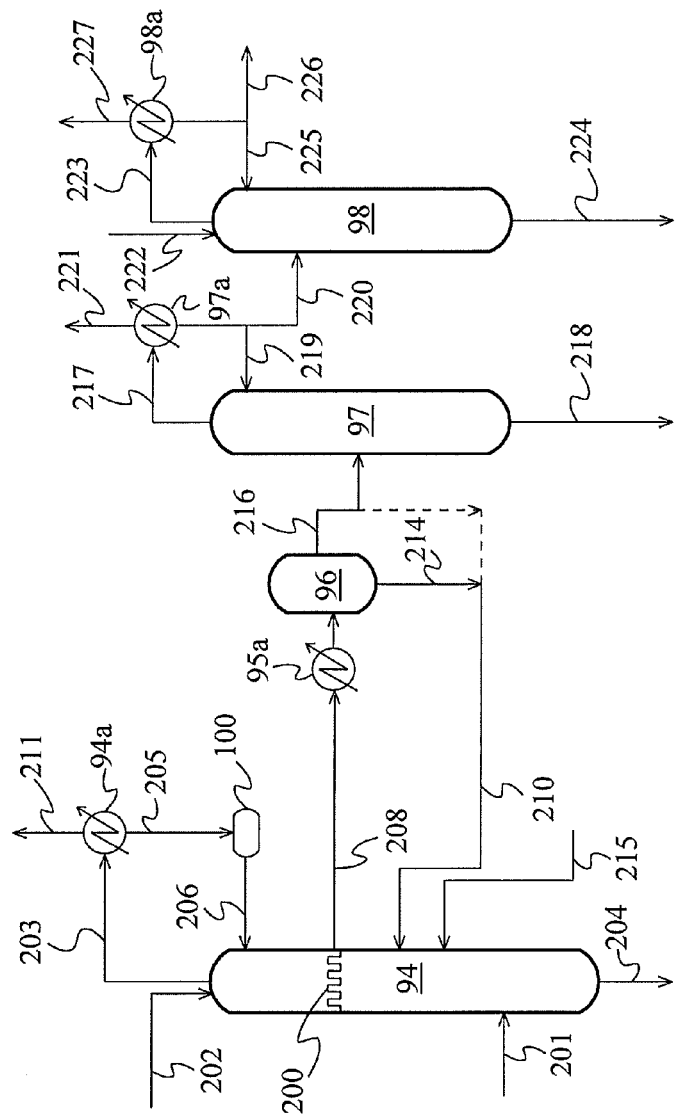

[Figure 6]
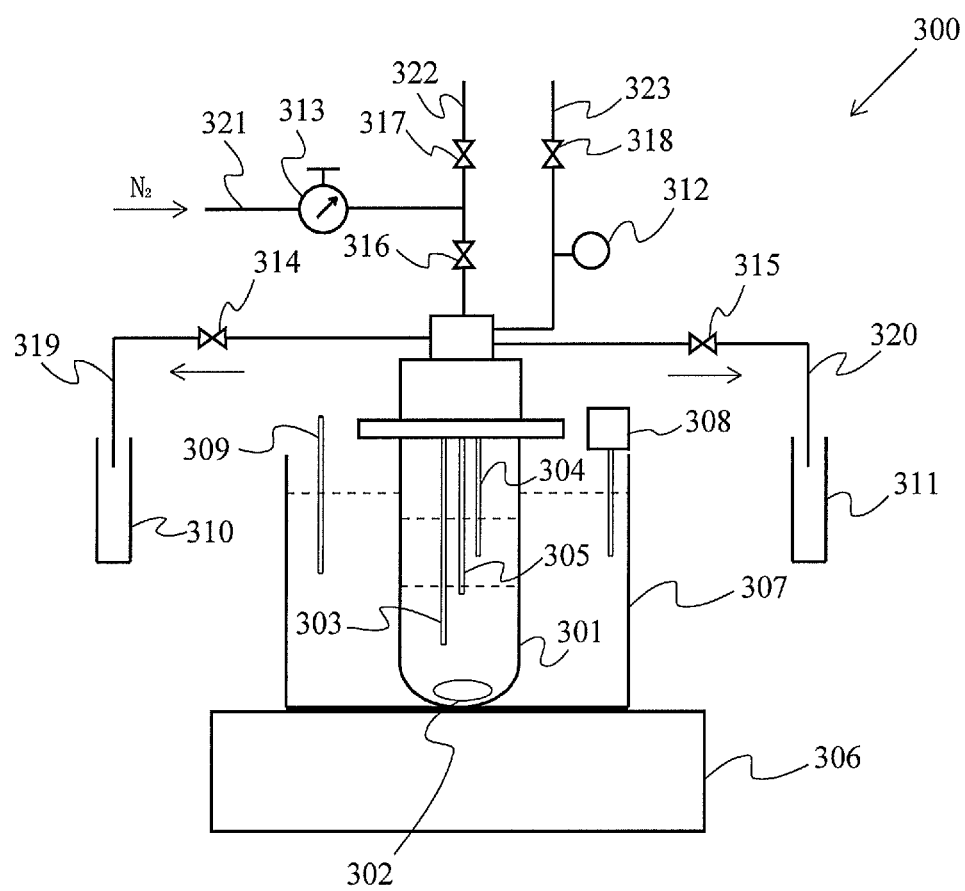

METHOD FOR PRODUCING ACETIC ACID

TECHNICAL FIELD

The present invention relates to a method for producing acetic acid. The present application claims the priorities of Japanese Patent Application No. 2017-006645 filed in Japan on Jan. 18, 2017 and Japanese Patent Application No. 2017-039389 filed in Japan on Mar. 2, 2017, the contents of which are incorporated herein by reference in their entirety.

BACKGROUND ART

A carbonylation process of a methanol method is known as an industrial method for producing acetic acid. In this process, for example, methanol and carbon monoxide are reacted in the presence of a catalyst in a reaction vessel to produce acetic acid. The obtained reaction mixture is separated in an evaporator into a vapor phase containing acetic acid and lower boiling point components and a residual liquid phase containing acetic acid and the catalyst, and the vapor phase is separated by distillation in a distillation column (lower boiling point component removal column) into an overhead stream containing lower boiling point components and an acetic acid stream. The acetic acid stream is further purified to obtain product acetic acid. In this process, acetaldehyde is produced as a by-product during the reaction, and this acetaldehyde is responsible for reducing the quality of the product acetic acid. Therefore, for example, in Patent Literature 1, a condensate of the overhead stream of the lower boiling point component removal column is separated into an aqueous phase and an organic phase using a decanter. Of them, the aqueous phase is distilled in an acetaldehyde removal column, and a condensate (containing acetaldehyde and methyl iodide) of an overhead stream thereof is subjected to extraction with water to thereby separate and remove acetaldehyde.

CITATION LIST

Patent Literature

Patent Literature 1: National Publication of International Patent Application No. 2001-508405

SUMMARY OF INVENTION

Technical Problem

According to the studies of the present inventors, a method of distilling, in an acetaldehyde removal column, an aqueous phase of two phases separated using a decanter in a lower boiling point component removal column as described in Patent Literature 1 mentioned above, generally tends to have high separation efficiency because the aqueous phase has a higher acetaldehyde concentration than that of the organic phase. However, in this method, treatment energy is increased for distilling a liquid containing a large amount of water having large latent heat of evaporation. In addition, a distillation apparatus made of an expensive material having very high corrosion resistance is necessary because hydrogen iodide formed by the hydrolysis of methyl iodide contained in a small amount in the aqueous phase easily corrodes a distillation apparatus. Since a considerable amount of methyl iodide is present in the aqueous phase, the number of plates of a distillation column equivalent to that in the case of distilling an organic phase (methyl iodide phase) in an acetaldehyde removal column as mentioned later is necessary for the separation of methyl iodide and acetaldehyde with small difference in boiling point in addition to the separation of water.

On the other hand, a method of distilling, in an acetaldehyde removal column, an organic phase of the two phases separated using the decanter in the lower boiling point component removal column, and subjecting a condensate of an overhead stream thereof to extraction with water to thereby separate and remove acetaldehyde is also known. This method has the advantages that: treatment energy is small because the main component of the organic phase is methyl iodide having small latent heat of evaporation; and the corrosion problem is also less likely to arise as compared with the case of treating the aqueous phase. However, as described above, according to the studies of the present inventors, there is the disadvantage that separation efficiency is generally low because the organic phase has a lower acetaldehyde concentration than that of the aqueous phase. Thus, both of the method of subjecting the aqueous phase to the acetaldehyde removal treatment and the method of subjecting the organic phase to the acetaldehyde removal treatment have advantages and disadvantages.

Thus, an object of the present invention is to provide a method capable of industrially advantageously separating and removing a by-product acetaldehyde in consideration of the advantages and disadvantages of the method of subjecting the aqueous phase to the acetaldehyde removal treatment and the method of subjecting the organic phase to the acetaldehyde removal treatment in the separation step of separating a process stream into the aqueous phase and the organic phase in the carbonylation process of the methanol method.

Solution to Problem

In order to attain the object, the present inventors have focused on an acetaldehyde distribution coefficient (acetaldehyde concentration in the aqueous phase/acetaldehyde concentration in the organic phase) under various conditions in the separation step, and conducted a liquid-liquid equilibrium experiment simulating the condensate composition of an overhead stream of a lower boiling point component removal column. As a result, the present inventors have found that there exists the given correlation of acetaldehyde concentrations in an aqueous phase and an organic phase obtained by separation using a decanter in the lower boiling point component removal column, a liquid temperature at the time of the separation, and methyl acetate concentrations in the aqueous phase and the organic phase with the distribution coefficient of acetaldehyde. As mentioned above, the method of subjecting the aqueous phase to the acetaldehyde removal treatment and the method of subjecting the organic phase to the acetaldehyde removal treatment each have advantages and disadvantages. Therefore, it is industrially advantageous to adopt the former method in the case where the acetaldehyde distribution coefficient is high to some extent (in the case where acetaldehyde is distributed in a relatively large amount in the aqueous phase), to adopt the latter method in the case where the acetaldehyde distribution coefficient is low to some extent (in the case where acetaldehyde is distributed in a relatively large amount in the organic phase), and to adopt both the methods for an intermediate region thereof. Particularly, for adopting the method of subjecting the aqueous phase to the acetaldehyde removal treatment, it is necessary to use an expensive apparatus or equipment having high corrosion resistance.

Therefore, it is necessary to strictly determine the acetaldehyde distribution coefficient. The present invention is based on these findings and discussions and has been completed through further studies.

Specifically, the present invention provides a method for producing acetic acid, comprising:

a carbonylation reaction step of reacting methanol with carbon monoxide in the presence of a catalyst system comprising a metal catalyst and methyl iodide, acetic acid, methyl acetate, and water in a reaction vessel to produce acetic acid;

an evaporation step of separating the reaction mixture obtained in the carbonylation reaction step into a vapor stream and a residual liquid stream in an evaporator;

a lower boiling point component removal step of separating the vapor stream by distillation into an overhead stream rich in at least one lower boiling point component selected from methyl iodide and acetaldehyde and an acetic acid stream rich in acetic acid;

a separation step of separating a process stream containing at least water, acetic acid, methyl iodide, and acetaldehyde into an aqueous phase and an organic phase; and an acetaldehyde separation and removal step for separating and removing the acetaldehyde derived from the process stream, wherein the separation step satisfies at least one of the following conditions (i) to (v), and at least a portion of the organic phase is treated in the acetaldehyde separation and removal step (hereinafter, this method is also referred to as the "production method 1 of the present invention"):

(i) an acetaldehyde concentration in the aqueous phase is not less than 0.045% by mass, and/or an acetaldehyde concentration in the organic phase is not less than 0.013% by mass;

(ii) a temperature at the time of the separation is not less than −5° C.;

(iii) a methyl acetate concentration in the aqueous phase is not less than 1.2% by mass, and/or a methyl acetate concentration in the organic phase is not less than 2.2% by mass, and/or the sum of the methyl acetate concentration in the aqueous phase and the methyl acetate concentration in the organic phase is not less than 3.4% by mass;

(iv) an acetaldehyde distribution coefficient [{acetaldehyde concentration (% by mass) of the aqueous phase}/{acetaldehyde concentration (% by mass) of the organic phase}] is not more than 4.1; and (v) a methyl acetate distribution coefficient [{methyl acetate concentration (% by mass) of the aqueous phase}/{methyl acetate concentration (% by mass) of the organic phase}] is not more than 0.53.

In the production method 1 of the present invention, the catalyst system may further comprise an ionic iodide.

In the production method 1 of the present invention, it is preferred that the separation step should satisfy all of the conditions (i), (ii), (iii), (iv), and (v).

The present invention also provides a method for producing acetic acid by reacting methanol with carbon monoxide in the presence of a catalyst system comprising a metal catalyst and methyl iodide, acetic acid, methyl acetate, and water, comprising:

a separation step of separating a process stream containing at least water, acetic acid, methyl iodide, and acetaldehyde into an aqueous phase and an organic phase; and an acetaldehyde separation and removal step for separating and removing the acetaldehyde derived from the process stream, wherein the separation step satisfies at least one of the following conditions (i) to (v), and at least a portion of the organic phase is treated in the acetaldehyde separation and removal step (hereinafter, this method is also referred to as the "production method 2 of the present invention"):

(i) an acetaldehyde concentration in the aqueous phase is not less than 0.045% by mass, and/or an acetaldehyde concentration in the organic phase is not less than 0.013% by mass;

(ii) a temperature at the time of the separation is not less than −5° C.;

(iii) a methyl acetate concentration in the aqueous phase is not less than 1.2% by mass, and/or a methyl acetate concentration in the organic phase is not less than 2.2% by mass, and/or the sum of the methyl acetate concentration in the aqueous phase and the methyl acetate concentration in the organic phase is not less than 3.4% by mass;

(iv) an acetaldehyde distribution coefficient [{acetaldehyde concentration (% by mass) of the aqueous phase}/{acetaldehyde concentration (% by mass) of the organic phase}] is not more than 4.1; and (v) a methyl acetate distribution coefficient [{methyl acetate concentration (% by mass) of the aqueous phase}/{methyl acetate concentration (% by mass) of the organic phase}] is not more than 0.53.

In the production method 2 of the present invention, the catalyst system may further comprise an ionic iodide.

In the production method 2 of the present invention, it is preferred that the separation step should satisfy all of the conditions (i), (ii), (iii), (iv), and (v).

The present invention further provides a method for producing acetic acid, comprising:

a carbonylation reaction step of reacting methanol with carbon monoxide in the presence of a catalyst system comprising a metal catalyst and methyl iodide, acetic acid, methyl acetate, and water in a reaction vessel to produce acetic acid;

an evaporation step of separating the reaction mixture obtained in the carbonylation reaction step into a vapor stream and a residual liquid stream in an evaporator;

a lower boiling point component removal step of separating the vapor stream by distillation into an overhead stream rich in at least one lower boiling point component selected from methyl iodide and acetaldehyde and an acetic acid stream rich in acetic acid;

a separation step of separating a process stream containing at least water, acetic acid, methyl iodide, and acetaldehyde into an aqueous phase and an organic phase; and an acetaldehyde separation and removal step for separating and removing the acetaldehyde derived from the process stream, wherein the separation step satisfies at least one of the following conditions (vi) to (x), and at least a portion of the aqueous phase is treated in the acetaldehyde separation and removal step (hereinafter, this method is also referred to as the "production method 3 of the present invention"):

(vi) an acetaldehyde concentration in the aqueous phase is not more than 28.1% by mass, and/or an acetaldehyde concentration in the organic phase is not more than 24.8% by mass;

(vii) a temperature at the time of the separation is not more than 70° C.;

(viii) a methyl acetate concentration in the aqueous phase is not more than 12.0% by mass, and/or a methyl acetate concentration in the organic phase is not more than 47.6% by mass, and/or the sum of the methyl acetate concentration in the aqueous phase and the methyl acetate concentration in the organic phase is not more than 59.6% by mass;

(ix) an acetaldehyde distribution coefficient [{acetaldehyde concentration (% by mass) of the aqueous phase}/{acetaldehyde concentration (% by mass) of the organic phase}] is not less than 1.1; and (x) a methyl acetate distribution coefficient [{methyl acetate concentration (% by mass) of the aqueous phase}/{methyl acetate concentration (% by mass) of the organic phase}] is not less than 0.25.

In the production method 3 of the present invention, the catalyst system may further comprise an ionic iodide.

In the production method 3 of the present invention, it is preferred that the separation step should satisfy all of the conditions (vi), (vii), (viii), (ix), and (x).

The present invention further provides a method for producing acetic acid by reacting methanol with carbon monoxide in the presence of a catalyst system comprising a metal catalyst and methyl iodide, acetic acid, methyl acetate, and water, comprising a separation step of separating a process stream containing at least water, acetic acid, methyl iodide, and acetaldehyde into an aqueous phase and an organic phase; and an acetaldehyde separation and removal step for separating and removing the acetaldehyde derived from the process stream, wherein the separation step satisfies at least one of the following conditions (vi) to (x), and at least a portion of the aqueous phase is treated in the acetaldehyde separation and removal step (hereinafter, this method is also referred to as the "production method 4 of the present invention"):

(vi) an acetaldehyde concentration in the aqueous phase is not more than 28.1% by mass, and/or an acetaldehyde concentration in the organic phase is not more than 24.8% by mass;

(vii) a temperature at the time of the separation is not more than 70° C.;

(viii) a methyl acetate concentration in the aqueous phase is not more than 12.0% by mass, and/or a methyl acetate concentration in the organic phase is not more than 47.6% by mass, and/or the sum of the methyl acetate concentration in the aqueous phase and the methyl acetate concentration in the organic phase is not more than 59.6% by mass;

(ix) an acetaldehyde distribution coefficient [{acetaldehyde concentration (% by mass) of the aqueous phase}/{acetaldehyde concentration (% by mass) of the organic phase}] is not less than 1.1; and (x) a methyl acetate distribution coefficient [{methyl acetate concentration (% by mass) of the aqueous phase}/{methyl acetate concentration (% by mass) of the organic phase}] is not less than 0.25.

In the production method 4 of the present invention, the catalyst system may further comprise an ionic iodide.

In the production method 4 of the present invention, it is preferred that the separation step should satisfy all of the conditions (vi), (vii), (viii), (ix), and (x).

The production methods 1 to 4 of the present invention may further comprise a scrubber step of separating offgas from the process into a stream rich in carbon monoxide and a stream rich in acetic acid by absorption treatment with an absorption solvent containing at least acetic acid.

Advantageous Effects of Invention

According to the present invention, in the separation step of separating a process stream into an aqueous phase and an organic phase, an object to be subjected to acetaldehyde removal treatment is determined on the basis of an acetaldehyde concentration in the aqueous phase, an acetaldehyde concentration in the organic phase, a temperature at the time of the separation, a methyl acetate concentration in the aqueous phase, or a methyl acetate concentration in the organic phase, etc. Therefore, acetaldehyde produced as a by-product in the carbonylation process of the methanol method can be removed industrially advantageously and efficiently.

BRIEF DESCRIPTION OF DRAWINGS

FIG. 1 is an acetic acid production flow diagram showing one embodiment of the present invention.

FIG. 2 is a schematic flow diagram showing one example of an acetaldehyde separation and removal system.

FIG. 3 is a schematic flow diagram showing another example of the acetaldehyde separation and removal system.

FIG. 4 is a schematic flow diagram showing a further alternative example of the acetaldehyde separation and removal system.

FIG. 5 is a schematic flow diagram showing a further alternative example of the acetaldehyde separation and removal system.

FIG. 6 is a schematic diagram of a liquid-liquid equilibrium measurement apparatus used in Examples of the present invention.

DESCRIPTION OF EMBODIMENTS

FIG. 1 is an acetic acid production flow diagram showing one embodiment of the present invention. An acetic acid production apparatus associated with this acetic acid production flow has a reaction vessel 1, an evaporator 2, a distillation column 3, a decanter 4, a distillation column 5, a distillation column 6, an ion exchange resin column 7, a scrubber system 8, an acetaldehyde separation and removal system 9, condensers 1a, 2a, 3a, 5a, and 6a, a heat exchanger 2b, reboilers 3b, 5b, and 6b, lines 11 to 56, and a pump 57 and is configured to be capable of continuously producing acetic acid. In the method for producing acetic acid according to the present embodiment, a reaction step, an evaporation step (flash step), a first distillation step, a second distillation step, a third distillation step, and an adsorptive removal step are performed in the reaction vessel 1, the evaporator 2, the distillation column 3, the distillation column 5, the distillation column 6, and the ion exchange resin column 7, respectively. The first distillation step is also referred to as a lower boiling point component removal step, the second distillation step is also referred to as a dehydration step, and the third distillation step is also referred to as a higher boiling point component removal step. Also, a separation step and an acetaldehyde separation and removal (acetaldehyde removal treatment) step are performed in the decanter 4 and the acetaldehyde separation and removal system 9, respectively. In the present invention, the steps are not limited to those described above and may exclude, particularly, equipment of the distillation column 5, distillation column 6, the ion exchange resin column 7.

The reaction vessel 1 is a unit for performing the reaction step. This reaction step is a step for continuously producing acetic acid through a reaction (methanol carbonylation reaction) represented by the chemical formula (1) given below. In a steady operation state of the acetic acid production apparatus, for example, a reaction mixture under stirring with a stirrer is present in the reaction vessel 1. The reaction mixture contains methanol and carbon monoxide which are raw materials, a metal catalyst, a co-catalyst, water, a production target acetic acid, and various by-products, and a liquid phase and a gaseous phase are in equilibrium.

$$CH_3OH + CO \rightarrow CH_3COOH \quad (1)$$

The raw materials in the reaction mixture are methanol in a liquid state and carbon monoxide in a gaseous state. Methanol is continuously fed at a predetermined flow rate to the reaction vessel 1 from a methanol reservoir (not shown) through the line 11. Carbon monoxide is continuously fed at a predetermined flow rate to the reaction vessel 1 from a carbon monoxide reservoir (not shown) through the line 12. The carbon monoxide is not necessarily required to be pure carbon monoxide and may contain, for example, other gases such as nitrogen, hydrogen, carbon dioxide, and oxygen, in a small amount (e.g., not more than 5% by mass, preferably not more than 1% by mass).

The metal catalyst in the reaction mixture promotes the carbonylation reaction of methanol, and, for example, a rhodium catalyst or an iridium catalyst can be used. For example, a rhodium complex represented by the chemical formula [Rh(CO)$_2$I$_2$]$^-$ can be used as the rhodium catalyst. For example, an iridium complex represented by the chemical formula [Ir(CO)$_2$I$_2$]$^-$ can be used as the iridium catalyst. A metal complex catalyst is preferred as the metal catalyst. The concentration (in terms of the metal) of the catalyst in the reaction mixture is, for example, 200 to 5000 ppm by mass, preferably 400 to 2000 ppm by mass, with respect to the whole liquid phase of the reaction mixture.

The co-catalyst is an iodide for assisting the action of the catalyst mentioned above, and, for example, methyl iodide or an ionic iodide is used. The methyl iodide can exhibit the effect of promoting the catalytic effect of the catalyst mentioned above. The concentration of the methyl iodide is, for example, 1 to 20% by mass with respect to the whole liquid phase of the reaction mixture. The ionic iodide is an iodide that generates iodide ions in a reaction solution (particularly, an ionic metal iodide) and can exhibit the effect of stabilizing the catalyst mentioned above and the effect of suppressing side reaction. Examples of the ionic iodide include alkali metal iodides such as lithium iodide, sodium iodide, and potassium iodide. The concentration of the ionic iodide in the reaction mixture is, for example, 1 to 25% by mass, preferably 5 to 20% by mass, with respect to the whole liquid phase of the reaction mixture. In addition, when an iridium catalyst or the like is used, for example, a ruthenium compound or an osmium compound can be used as a co-catalyst. The amount of these compounds to be used as the total amount is, for example 0.1 to 30 moles (in terms of metal), preferably 0.5 to 15 moles (in terms of metal) based on 1 mole of iridium (in terms of metal).

Water in the reaction mixture is a component necessary for generating acetic acid in the reaction mechanism of the methanol carbonylation reaction and is also a component necessary for solubilizing a water-soluble component in the reaction system. The concentration of water in the reaction mixture is, for example, 0.1 to 15% by mass, preferably 0.8 to 10% by mass, further preferably 1 to 6% by mass, particularly preferably 1.5 to 4% by mass, with respect to the whole liquid phase of the reaction mixture. The water concentration is preferably not more than 15% by mass for pursuing efficient acetic acid production by reducing energy required for the removal of water in the course of purification of acetic acid. In order to control the water concentration, water may be continuously fed at a predetermined flow rate to the reaction vessel 1.

The acetic acid in the reaction mixture includes acetic acid fed in advance into the reaction vessel 1 before operation of the acetic acid production apparatus, and acetic acid generated as a main product of the methanol carbonylation reaction. Such acetic acid can function as a solvent in the reaction system. The concentration of the acetic acid in the reaction mixture is, for example, 50 to 90% by mass, preferably 60 to 80% by mass, with respect to the whole liquid phase of the reaction mixture.

Examples of the main by-products contained in the reaction mixture include methyl acetate. This methyl acetate may be generated through the reaction between acetic acid and methanol. The concentration of the methyl acetate in the reaction mixture is, for example, 0.1 to 30% by mass, preferably 1 to 10% by mass, with respect to the whole liquid phase of the reaction mixture. Another example of the by-products contained in the reaction mixture includes hydrogen iodide. This hydrogen iodide is inevitably generated under the reaction mechanism of the methanol carbonylation reaction in the case where the catalyst or the co-catalyst as mentioned above is used. The concentration of the hydrogen iodide in the reaction mixture is, for example, 0.01 to 2% by mass with respect to the whole liquid phase of the reaction mixture. Other examples of the by-products include hydrogen, methane, carbon dioxide, acetaldehyde, crotonaldehyde, 2-ethyl crotonaldehyde, dimethyl ether, alkanes, formic acid, propionic acid, and alkyl iodides such as hexyl iodide and decyl iodide. Also, the reaction mixture may contain a metal, such as iron, nickel, chromium, manganese, or molybdenum, generated by the corrosion of the apparatus (hereinafter, also referred to as a "corroded metal"), and other metals such as cobalt, zinc, and copper. The corroded metal and other metals are also collectively referred to as a "corroded metal, etc.".

In the reaction vessel 1 where the reaction mixture as described above is present, the reaction temperature is set to, for example, 150 to 250° C. The reaction pressure as the total pressure is set to, for example, 2.0 to 3.5 MPa (absolute pressure), and the carbon monoxide partial pressure is set to, for example, 0.4 to 1.8 MPa (absolute pressure), preferably 0.6 to 1.5 MPa (absolute pressure).

The vapor of a gaseous phase portion in the reaction vessel 1 during apparatus operation contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, formic acid, and propionic acid. This vapor can be withdrawn from the reaction vessel 1 through the line 13. The internal pressure of the reaction vessel 1 can be controlled by the adjustment of the amount of the vapor withdrawn, and, for example, the internal pressure of the reaction vessel 1 is kept constant. The vapor withdrawn from the reaction vessel 1 is introduced to the condenser 1$a$.

The condenser 1$a$ separates the vapor from the reaction vessel 1 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, formic acid, and propionic acid and is introduced to the reaction vessel 1 from the condenser 1$a$ through the line 14 and recycled. The gaseous portion contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 1$a$ through the line 15. In the scrubber system 8, useful components (e.g., methyl iodide, water, methyl acetate, and acetic acid) are separated and recovered from the gaseous portion from the condenser 1a. In this separation and recovery, a wet method that is performed using an absorbing liquid for capturing the useful components in the gaseous portion is utilized in the present embodiment. An absorption solvent containing at least acetic acid and/or methanol is preferred as the absorbing liquid. The absorbing liquid may contain methyl acetate. For example, a condensate portion of a vapor from the distillation column 6 mentioned later can be used as the absorbing liquid. In the separation and recovery, a pressure swing adsorption method may be used. The separated and recovered useful components (e.g., methyl iodide) are introduced to the reaction vessel 1 from the scrubber system 8 through the recycle line 48 and recycled. A gas after the capturing of the useful components is discarded through the line 49. The gas discharged from the line 49 can be used as a CO source to be introduced to the bottom part of the evaporator 2 mentioned later or the residual liquid stream recycle lines 18 and 19. As for treatment in the scrubber system 8 and subsequent recycle to the reaction vessel 1 and discarding, the same holds true for gaseous portions described later that are fed to the scrubber system 8 from other condensers. For the production method of the present invention, it is preferred to have a scrubber step of separating offgas from the process into a stream rich in carbon monoxide and a stream rich in acetic acid by absorption treatment with an absorption solvent containing at least acetic acid.

In the reaction vessel 1 during apparatus operation, as mentioned above, acetic acid is continuously produced. The reaction mixture containing such acetic acid is continuously withdrawn at a predetermined flow rate from the reaction vessel 1 and introduced to the next evaporator 2 through the line 16.

The evaporator 2 is a unit for performing the evaporation step (flash step). This evaporation step is a step for separating the reaction mixture continuously introduced to the evaporator 2 through the line 16 (reaction mixture feed line), into a vapor stream (volatile phase) and a residual liquid stream (low volatile phase) by partial evaporation. The evaporation may be caused by reducing the pressure without heating the reaction mixture, or the evaporation may be caused by reducing the pressure while heating the reaction mixture. In the evaporation step, the temperature of the vapor stream is, for example, 100 to 260° C., preferably 120 to 200° C., and the temperature of the residual liquid stream is, for example, 80 to 200° C., preferably 100 to 180° C. The internal pressure of the evaporator is, for example, 50 to 1000 kPa (absolute pressure). The ratio between the vapor stream and the residual liquid stream to be separated in the evaporation step is, for example, 10/90 to 50/50 (vapor stream/residual liquid stream) in terms of a mass ratio. The vapor generated in this step contains, for example, methyl iodide, hydrogen iodide, water, methyl acetate, acetic acid, dimethyl ether, methanol, acetaldehyde, formic acid, and propionic acid and is continuously withdrawn to the line 17 (vapor stream discharge line) from the evaporator 2. A portion of the vapor stream withdrawn from the evaporator 2 is continuously introduced to the condenser 2a, and another portion of the vapor stream is continuously introduced to the next distillation column 3 through the line 21. The vapor stream has an acetic acid concentration of, for example, 40 to 85% by mass (preferably 50 to 85% by mass), further preferably 50 to 75% by mass (e.g., 55 to 75% by mass), a methyl iodide concentration of, for example, 2 to 50% by mass (preferably 5 to 30% by mass), a water concentration of, for example, 0.2 to 20% by mass (preferably 1 to 15% by mass), and a methyl acetate concentration of, for example, 0.2 to 50% by mass (preferably 2 to 30% by mass). The residual liquid stream generated in this step contains, for example, the catalyst and the co-catalyst (methyl iodide, lithium iodide, etc.) contained in the reaction mixture, and water, methyl acetate, acetic acid, formic acid, and propionic acid remaining without being volatilized in this step, and is continuously introduced to the heat exchanger 2b from the evaporator 2 through the line 18 using the pump 57. The heat exchanger 2b cools the residual liquid stream from the evaporator 2. The cooled residual liquid stream is continuously introduced to the reaction vessel 1 from the heat exchanger 2b through the line 19 and recycled. The line 18 and the line 19 are collectively referred to as residual liquid stream recycle lines. The acetic acid concentration of the residual liquid stream is, for example, 55 to 90% by mass, preferably 60 to 85% by mass.

It is preferred to connect a carbon monoxide-containing gas introduction line 54 for introducing a carbon monoxide-containing gas to the bottom of the evaporator 2 and/or the residual liquid stream recycle lines (line 18 and/or line 19). Carbon monoxide is introduced to a residual liquid retained in the lower part of the evaporator 2 or to a residual liquid stream passing through the residual liquid stream recycle lines 18 and 19 (particularly, the line 18) to thereby increase the amount of carbon monoxide dissolved in the residual liquid stream. Thus, the stability of the catalyst is enhanced, and the precipitation or accumulation of the catalyst can be prevented. The content of the carbon monoxide in the carbon monoxide-containing gas to be introduced is, for example, not less than 10% by mass, preferably not less than 20% by mass, further preferably not less than 40% by mass, particularly preferably not less than 60% by mass.

The condenser 2a separates the vapor stream from the evaporator 2 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, formic acid, and propionic acid and is introduced to the reaction vessel 1 from the condenser 2a through the lines 22 and 23 and recycled. The gaseous portion contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 2a through the lines 20 and 15. Since the reaction to produce acetic acid in the reaction step mentioned above is an exothermic reaction, a portion of heat accumulated in the reaction mixture is transferred to the vapor generated from the reaction mixture in the evaporation step (flash step). The condensate portion generated by the cooling of this vapor in the condenser 2a is recycled to the reaction vessel 1. Specifically, in this acetic acid production apparatus, heat generated through the methanol carbonylation reaction is efficiently removed in the condenser 2a.

The distillation column 3 is a unit for performing the first distillation step and serves as the so-called lower boiling point component removal column in the present embodiment. The first distillation step is the step of subjecting the vapor stream continuously introduced to the distillation column 3 to distillation treatment to separate and remove lower boiling point components. More specifically, in the first distillation step, the vapor stream is separated by distillation into an overhead stream rich in at least one lower boiling point component selected from methyl iodide and acetaldehyde, and an acetic acid stream rich in acetic acid.

The distillation column 3 consists of, for example, a distillation column such as a plate column or a packed column. In the case of adopting a plate column as the distillation column 3, the theoretical number of plates thereof is, for example, 5 to 50, and the reflux ratio is, for example, 0.5 to 3000 according to the theoretical number of plates. In the inside of the distillation column 3, the column top pressure is set to, for example, 80 to 160 kPa (gauge pressure), and the column bottom pressure is higher than the column top pressure and is set to, for example, 85 to 180 kPa (gauge pressure). In the inside of the distillation column 3, the column top temperature is, for example, a temperature of lower than the boiling point of acetic acid at the set column top pressure and is set to 90 to 130° C., and the column bottom temperature is, for example, a temperature of not less than the boiling point of acetic acid at the set column bottom pressure and is set to 120 to 160° C.

The vapor stream from the evaporator 2 is continuously introduced to the distillation column 3 through the line 21. From the column top of the distillation column 3, a vapor as the overhead stream is continuously withdrawn to the line 24. From the column bottom of the distillation column 3, a bottom fraction is continuously withdrawn to the line 25. 3b denotes a reboiler. From the height position between the column top and the column bottom of the distillation column 3, the acetic acid stream (first acetic acid stream; liquid) as a side stream is continuously withdrawn through the line 27.

The vapor withdrawn from the column top of the distillation column 3 contains a larger amount of components having a lower boiling point (lower boiling point components) than that of acetic acid as compared with the bottom fraction and the side stream from the distillation column 3 and contains, for example, methyl iodide, hydrogen iodide, water, methyl acetate, dimethyl ether, methanol, acetaldehyde, and formic acid. This vapor also contains acetic acid. Such a vapor is continuously introduced to the condenser 3a through the line 24.

The condenser 3a separates the vapor from the distillation column 3 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, and formic acid and is continuously introduced to the decanter 4 from the condenser 3a through the line 28. The condensate portion introduced to the decanter 4 is separated into an aqueous phase (upper phase) and an organic phase (methyl iodide phase; lower phase). The aqueous phase contains water and, for example, methyl iodide, hydrogen iodide, methyl acetate, acetic acid, dimethyl ether, methanol, acetaldehyde, and formic acid. The organic phase contains, for example, methyl iodide and, for example, hydrogen iodide, water, methyl acetate, acetic acid, dimethyl ether, methanol, acetaldehyde, and formic acid. In the present embodiment, a portion of the aqueous phase is refluxed to the distillation column 3 through the line 29, and another portion of the aqueous phase is introduced to the reaction vessel 1 through the lines 29, 30, and 23 and recycled. A portion of the organic phase is introduced to the reaction vessel 1 through the lines 31 and 23 and recycled. Another portion of the organic phase and/or a remaining portion of the aqueous phase is introduced to the acetaldehyde separation and removal system 9 through the lines 31 and 50 and/or the lines 30 and 51.

In the present invention, in the separation step (e.g., separation in the decanter 4) of separating a process stream containing at least water, acetic acid (AC), methyl iodide (MeI), and acetaldehyde (AD) into an aqueous phase and an organic phase, a phase to be subjected to the acetaldehyde separation and removal step is determined on the basis of an acetaldehyde concentration in the aqueous phase, an acetaldehyde concentration in the organic phase, a methyl acetate concentration in the aqueous phase, a methyl acetate concentration in the organic phase, the sum of the methyl acetate concentration in the aqueous phase and the methyl acetate concentration in the organic phase, a temperature (liquid temperature) at the time of the separation, an acetaldehyde distribution coefficient (AD distribution coefficient) determined according to the expression given below, or a methyl acetate distribution coefficient (MA distribution coefficient) determined according to the expression given below. In another aspect, a preferred separation condition for subjecting the organic phase to the acetaldehyde separation and removal step, and a preferred separation condition for subjecting the aqueous phase to the acetaldehyde separation and removal step are shown.

AD distribution coefficient={AD concentration (% by mass) of the aqueous phase}/{AD concentration (% by mass) of the organic phase}

MA distribution coefficient={MA concentration (% by mass) of the aqueous phase}/{MA concentration (% by mass) of the organic phase}

In the production methods 1 and 2 of the present invention, the separation step satisfies at least one of the following conditions (i) to (v), and at least a portion of the organic phase is treated in the acetaldehyde separation and removal step:

(i) an acetaldehyde concentration in the aqueous phase is not less than 0.045% by mass, and/or an acetaldehyde concentration in the organic phase is not less than 0.013% by mass;

(ii) a temperature at the time of the separation is not less than $-5°$ C.;

(iii) a methyl acetate concentration in the aqueous phase is not less than 1.2% by mass, and/or a methyl acetate concentration in the organic phase is not less than 2.2% by mass, and/or the sum of the methyl acetate concentration in the aqueous phase and the methyl acetate concentration in the organic phase is not less than 3.4% by mass;

(iv) an acetaldehyde distribution coefficient [{acetaldehyde concentration (% by mass) of the aqueous phase}/{acetaldehyde concentration (% by mass) of the organic phase}] is not more than 4.1; and (v) a methyl acetate distribution coefficient [{methyl acetate concentration (% by mass) of the aqueous phase}/{methyl acetate concentration (% by mass) of the organic phase}] is not more than 0.53.

In the condition (i), the acetaldehyde concentration in the aqueous phase is, for example, 0.045 to 35% by mass, preferably 0.15 to 10% by mass, further preferably 0.2 to 2.0% by mass. Also, the acetaldehyde concentration in the organic phase is, for example, 0.013 to 30% by mass, preferably 0.05 to 5.0% by mass, further preferably 0.1 to 1.0% by mass. In the condition (i), it is preferred that the acetaldehyde concentration in the aqueous phase should be not less than 0.045% by mass, and the acetaldehyde concentration in the organic phase should be not less than 0.013% by mass. In the condition (i), an acetaldehyde concentration in a liquid to be subjected to the separation (hereinafter, also referred to as a "separation step feeding liquid"; e.g., a liquid to be fed to the decanter 4) is, for example, not less than 0.026% by mass (e.g., 0.026 to 32% by mass), preferably 0.10 to 8.0% by mass, further preferably 0.15 to 1.8% by mass. In the case where the acetaldehyde concentration in the aqueous phase is less than 0.045% by mass or in the case where the acetaldehyde concentration in the organic phase is less than 0.013% by mass, it is very low advantageous to treat the organic phase in the acetaldehyde separation and removal step because the AD distribution coefficient is a large value.

In the condition (ii), the temperature (liquid temperature) at the time of the separation is not less than −5° C. (e.g., −5° C. to 90° C.), preferably not less than 0° C. (e.g., 0 to 90° C.), further preferably not less than 10° C. (e.g., 10 to 90° C.), particularly preferably a temperature of higher than 70° C. (e.g., more than 70° C. and not more than 90° C.). In the case where the temperature (liquid temperature) at the time of the separation is less than −5° C., it is very low advantageous to treat the organic phase in the acetaldehyde separation and removal step because the AD distribution coefficient is, for example, more than 4.3.

In the condition (iii), the methyl acetate concentration in the aqueous phase is, for example, 1.2 to 15% by mass, preferably 2.5 to 12% by mass, further preferably 6.0 to 11% by mass. Also, the methyl acetate concentration in the organic phase is, for example, 2.2 to 60% by mass, preferably 5.8 to 48% by mass, further preferably 19 to 42% by mass. In the condition (iii), it is preferred that the methyl acetate concentration in the aqueous phase should be not less than 1.2% by mass, and the methyl acetate concentration in the organic phase should be not less than 2.2% by mass. Also, the sum of the methyl acetate concentration (% by mass) in the aqueous phase and the methyl acetate concentration (% by mass) in the organic phase is, for example, 3.4 to 75% by mass, preferably 8.3 to 60% by mass (e.g., 10 to 40% by mass), further preferably 25 to 53% by mass. In the case of the condition (iii), a methyl acetate concentration in the separation step feeding liquid (e.g., a liquid to be fed to the decanter 4) is, for example, 2.0 to 50% by mass, preferably 5.0 to 38% by mass, further preferably 15 to 31% by mass. In the case where the methyl acetate concentration in the aqueous phase is less than 1.2% by mass, in the case where the methyl acetate concentration in the organic phase is less than 2.2% by mass, or in the case where the sum of the methyl acetate concentration (% by mass) in the aqueous phase and the methyl acetate concentration (% by mass) in the organic phase is less than 3.4% by mass, it is low advantageous to treat the organic phase in the acetaldehyde separation and removal step because the AD distribution coefficient is a large value.

In the condition (iv), the AD distribution coefficient is not more than 4.1 (e.g., 0.5 to 4.1), preferably not more than 3.35 (e.g., 0.6 to 3.35), more preferably less than 1.5 (e.g., not less than 0.7 and less than 1.5), further preferably less than 1.1 (e.g., not less than 0.8 and less than 1.1). In the case where the AD distribution coefficient is more than 4.1, it is very low advantageous to treat the organic phase in the acetaldehyde separation and removal step because the acetaldehyde concentration in the organic phase is very low. A method for attaining the AD distribution coefficient (less than 1.1) most preferred for the acetaldehyde removal treatment of the organic phase includes, for example, setting the acetaldehyde concentration in the aqueous phase to more than 28.1% by mass, setting the acetaldehyde concentration in the organic phase to more than 24.8% by mass, setting the acetaldehyde concentration in the separation step feeding liquid to more than 26.0% by mass, setting the temperature at the time of the separation to more than 70° C., setting the methyl acetate concentration in the aqueous phase to more than 12.0% by mass, setting the methyl acetate concentration in the organic phase to more than 47.6% by mass, and setting the methyl acetate concentration in the separation step feeding liquid to more than 38.2% by mass.

In the condition (v), the MA distribution coefficient is not more than 0.53 (e.g., 0.15 to 0.53), preferably not more than 0.44 (e.g., 0.20 to 0.44), further preferably less than 0.25 (e.g., not less than 0.20 and less than 0.25). The rates of distribution of methyl acetate (MA) to the aqueous phase and the organic phase vary depending on a temperature and composition (containing components such as acetic acid in addition to water and methyl iodide), and this also serves as a guideline for acetaldehyde distribution coefficient control.

In the production methods 1 and 2 of the present invention, the separation step can satisfy at least one of the conditions (i) to (v), but may satisfy not less than 2 of the conditions at the same time. Examples of the combination of not less than 2 conditions to be preferably satisfied at the same time include combinations of the conditions (i) and (ii), the conditions (i) and (iii), the conditions (i) and (iv), the conditions (i) and (v), the conditions (ii) and (iii), the conditions (ii) and (iv), the conditions (ii) and (v), the conditions (iii) and (iv), the conditions (iii) and (v), the conditions (iv) and (v), the conditions (i), (ii), and (iii), the conditions (i), (ii), and (iv), the conditions (i), (ii), and (v), the conditions (i), (iii), and (iv), the conditions (i), (iii), and (v), the conditions (i), (iv), and (v), the conditions (ii), (iii), and (iv), the conditions (ii), (iii), and (v), the conditions (ii), (iv), and (v), the conditions (iii), (iv), and (v), the conditions (i), (ii), (iii), and (iv), the conditions (i), (ii), (iii), and (v), the conditions (i), (iii), (iv), and (v), the conditions (ii), (iii), (iv), and (v), and the conditions (i), (ii), (iii), (iv), and (v). Among them, it is particularly preferred to satisfy at least the conditions (i), (ii), and (iii) at the same time, to satisfy at least the conditions (i), (ii), (iii) and (iv) at the same time, or to satisfy all of the conditions (i), (ii), (iii), (iv), and (v) at the same time.

On the other hand, in the production methods 3 and 4 of the present invention, the separation step satisfies at least one of the following conditions (vi) to (x), and at least a portion of the aqueous phase is treated in the acetaldehyde separation and removal step:

(vi) an acetaldehyde concentration in the aqueous phase is not more than 28.1% by mass, and/or an acetaldehyde concentration in the organic phase is not more than 24.8% by mass;

(vii) a temperature at the time of the separation is not more than 70° C.;

(viii) a methyl acetate concentration in the aqueous phase is not more than 12.0% by mass, and/or a methyl acetate concentration in the organic phase is not more than 47.6% by mass, and/or the sum of the methyl acetate concentration in the aqueous phase and the methyl acetate concentration in the organic phase is not more than 59.6% by mass;

(ix) an acetaldehyde distribution coefficient [{acetaldehyde concentration (% by mass) of the aqueous phase}/ {acetaldehyde concentration (% by mass) of the organic phase}] is not less than 1.1; and (x) a methyl acetate distribution coefficient [{methyl acetate concentration (% by mass) of the aqueous phase}/ {methyl acetate concentration (% by mass) of the organic phase}] is not less than 0.25.

In the condition (vi), the acetaldehyde concentration in the aqueous phase is, for example, 0.045 to 28.1% by mass, preferably 0.098 to 10% by mass, further preferably 0.098 to 3.0% by mass, particularly preferably 0.098 to 1.0% by mass (e.g., 0.15 to 0.9% by mass). Also, the acetaldehyde concentration in the organic phase is, for example, 0.013 to 24.8% by mass, preferably 0.030 to 2.0% by mass, further preferably 0.030 to 0.50% by mass, particularly preferably 0.030 to 0.24% by mass. In the condition (vi), it is preferred that the acetaldehyde concentration in the aqueous phase should be not more than 28.1% by mass, and the acetaldehyde concentration in the organic phase should be not more than 24.8% by mass. In the condition (vi), an acetaldehyde concentration in a separation step feeding liquid (e.g., a liquid to be fed to the decanter 4) is, for example, not more than 26.0% by mass (e.g., 0.026 to 26.0% by mass), preferably 0.057 to 10% by mass, further preferably 0.057 to 3.0% by mass, particularly preferably 0.057 to 1.0% by mass (e.g., 0.057 to 0.42% by mass). In the case where the acetaldehyde concentration in the aqueous phase is more than 28.1% by mass or in the case where the acetaldehyde concentration in the organic phase is more than 24.8% by mass, it is very low advantageous to treat the aqueous phase in the acetaldehyde separation and removal step by weighing the amount of acetaldehyde recovered and the need of using an expensive apparatus having very high corrosion resistance, because the AD distribution coefficient is small (e.g., less than 1.1).

In the condition (vii), the temperature (liquid temperature) at the time of the separation is, for example, −5° C. to 70° C., preferably −5° C. to 51° C., further preferably −5° C. to 41° C. (e.g., −5° C. to 31° C.). In the case where the temperature (liquid temperature) at the time of the separation is more than 70° C., it is very low advantageous to treat the aqueous phase in the acetaldehyde separation and removal step because the AD distribution coefficient is very small.

In the condition (viii), the methyl acetate concentration in the aqueous phase is, for example, 1.2 to 12.0% by mass, preferably 2.0 to 12.0% by mass, further preferably 5.0 to 12.0% by mass (e.g., 6.0 to 12.0% by mass). Also, the methyl acetate concentration in the organic phase is, for example, 2.2 to 47.6% by mass, preferably 5.0 to 42% by mass, further preferably 8.0 to 35% by mass (e.g., 10 to 30% by mass). In the condition (viii), it is preferred that the methyl acetate concentration in the aqueous phase should be not more than 12.0% by mass, and the methyl acetate concentration in the organic phase should be not more than 47.6% by mass. Also, the sum of the methyl acetate concentration (% by mass) in the aqueous phase and the methyl acetate concentration (% by mass) in the organic phase is, for example, not more than 59.6% by mass (e.g., 4.2 to 59.6% by mass), preferably 10 to 54% by mass, further preferably 14 to 47% by mass (e.g., 16 to 42% by mass). In the condition (viii), a methyl acetate concentration in the separation step feeding liquid (e.g., a liquid to be fed to the decanter 4) is, for example, not more than 38.2% by mass (e.g., 2.0 to 38.2% by mass), preferably 5.0 to 31% by mass, further preferably 10 to 25% by mass. In the case where the methyl acetate concentration in the aqueous phase is more than 12.0% by mass, in the case where the methyl acetate concentration in the organic phase is more than 47.6% by mass, or in the case where the sum of the methyl acetate concentration (% by mass) in the aqueous phase and the methyl acetate concentration (% by mass) in the organic phase is more than 59.6% by mass, it is very low advantageous to treat the aqueous phase in the acetaldehyde separation and removal step for the same reasons as above because the AD distribution coefficient is, for example, less than 1.1.

In the condition (ix), the AD distribution coefficient is, for example, 1.1 to 8.0, preferably 1.5 to 6.0, further preferably 1.9 to 5.0. In the case where the AD distribution coefficient is less than 1.1, it is industrially very disadvantageous to perform the acetaldehyde removal treatment of the aqueous phase which requires large energy and easily corrodes an apparatus because the acetaldehyde concentration in the aqueous phase is low. However, when the AD distribution coefficient is not less than 1.1 (preferably not less than 1.5, further preferably not less than 1.9), improvement in acetaldehyde separation and removal efficiency is highly advantageous even if an apparatus having high corrosion resistance is used.

In the condition (x), the MA distribution coefficient is not less than 0.25 (e.g., 0.25 to 0.70), preferably not less than 0.26 (e.g., 0.26 to 0.65), further preferably not less than 0.28 (e.g., 0.28 to 0.60). As mentioned above, the rates of distribution of methyl acetate (MA) to the aqueous phase and the organic phase vary depending on a temperature and composition (containing components such as acetic acid in addition to water and methyl iodide), and this also serves as a guideline for acetaldehyde distribution coefficient control.

In the production methods 3 and 4 of the present invention, the separation step can satisfy at least one of the conditions (vi) to (x), but may satisfy not less than 2 of the conditions at the same time. Examples of the combination of not less than 2 conditions to be preferably satisfied at the same time include combinations of the conditions (vi) and (vii), the conditions (vi) and (viii), the conditions (vi) and (ix), the conditions (vi) and (x), the conditions (vii) and (viii), the conditions (vii) and (ix), the conditions (vii) and (x), the conditions (viii) and (ix), the conditions (viii) and (x), the conditions (ix) and (x), the conditions (vi), (vii), and (viii), the conditions (vi), (vii), and (ix), the conditions (vi), (vii), and (x), the conditions (vi), (viii), and (ix), the conditions (vi), (viii), and (x), the conditions (vi), (ix), and (x), the conditions (vii), (viii), and (ix), the conditions (vii), (viii), and (x), the conditions (vii), (ix), and (x), the conditions (viii), (ix), and (x), the conditions (vi), (vii), (viii), and (ix), the conditions (vi), (vii), (viii), and (x), the conditions (vi), (vii), (ix), and (x), the conditions (vi), (viii), (ix), and (x), the conditions (vii), (viii), (ix), and (x), and the conditions (vi), (vii), (viii), (ix), and (x). Among them, it is particularly preferred to satisfy at least the conditions (vi), (vii), and (viii) at the same time, to satisfy at least the conditions (vi), (vii), (viii), and (ix) at the same time, or to satisfy all of the conditions (vi), (vii), (viii), (ix), and (x) at the same time.

The acetaldehyde concentrations and the methyl acetate concentrations in the aqueous phase and the organic phase are determined by the composition of the separation step feeding liquid and the temperature at the time of the separation. As the separation step feeding liquid has a higher acetaldehyde concentration, the acetaldehyde concentrations in the aqueous phase and the organic phase are higher. As the separation step feeding liquid has a higher methyl acetate concentration, the methyl acetate concentrations in the aqueous phase and the organic phase are higher. As shown in Examples, at a higher temperature at the time of the separation, the rate of distribution of acetaldehyde to the organic phase is relatively higher. Furthermore, the acetaldehyde concentration and the methyl acetate concentration in the separation step feeding liquid can be controlled by, for example, reaction conditions for the reaction vessel 1, evaporation conditions for the evaporator 2, and distillation conditions for the distillation column 3. In general, when the reaction mixture has a higher acetaldehyde concentration and methyl acetate concentration, the acetaldehyde concentration and the methyl acetate concentration in the separation step feeding liquid are respectively higher. The acetaldehyde concentration in the reaction mixture tends to be increased with increase in each of the reaction temperature, the hydrogen partial pressure, the methyl iodide concentration, the water concentration, the catalyst concentration, and the lithium iodide concentration in the reaction system and to be decreased with increase in each of the CO partial pressure and the methyl acetate concentration (see Japanese Patent Laid-Open No. 2006-182691). Since methyl acetate is formed through the esterification reaction between acetic acid and methanol, the methyl acetate concentration in the reaction mixture is increased with increase in each of the acetic acid concentration and the methanol concentration in the reaction system and decreased with increase in the water concentration. Thus, the composition of the separation step feeding liquid and by extension, the acetaldehyde concentrations and the methyl acetate concentrations in the aqueous phase and the organic phase can be adjusted by adjusting reaction conditions for the reaction vessel, and operating conditions in the evaporation step or the distillation step that is performed before the separation step.

In the acetaldehyde separation and removal step using the acetaldehyde separation and removal system 9, the acetaldehyde derived from the process stream containing at least the water, the acetic acid (AC), the methyl iodide (MeI), and the acetaldehyde (AD) is separated and removed. A method known in the art can be used as a method for separating and removing acetaldehyde. Acetaldehyde is separated and removed by, for example, distillation, extraction, or a combination thereof. The separated acetaldehyde is discharge to the outside of the apparatus through the line 53. The useful components (e.g., methyl iodide) contained in the organic phase and/or the aqueous phase are recycled to the reaction vessel 1 through the lines 52 and 23 and reused.

FIG. 2 is a schematic flow diagram showing one example of the acetaldehyde separation and removal system. According to this flow, in the case of treating, for example, the organic phase in the acetaldehyde separation and removal step, the organic phase is fed to a distillation column (first acetaldehyde removal column) 91 through a line 101 and separated by distillation into an overhead stream rich in acetaldehyde (line 102) and a residual liquid stream rich in methyl iodide (line 103). The overhead stream is condensed in a condenser 91a. A portion of the condensate is refluxed to the column top of the distillation column 91 (line 104), and the remaining portion of the condensate is fed to an extraction column 92 (line 105). The condensate fed to the extraction column 92 is subjected to extraction treatment with water introduced from a line 109. The extract obtained by the extraction treatment is fed to a distillation column (second acetaldehyde removal column) 93 through a line 107 and separated by distillation into an overhead stream rich in acetaldehyde (line 112) and a residual liquid stream rich in water (line 113). Then, the overhead stream rich in acetaldehyde is condensed in a condenser 93a. A portion of the condensate is refluxed to the column top of the distillation column 93 (line 114), and the remaining portion of the condensate is discharged to the outside of the system (line 115). The residual liquid stream rich in methyl iodide, which is a bottom fraction of the first acetaldehyde removal column 91, a raffinate rich in methyl iodide (line 108) obtained in the extraction column 92, and the residual liquid stream rich in water, which is a bottom fraction of the second acetaldehyde removal column 93 are recycled to the reaction vessel 1 through the lines 103, 111, and 113, respectively, or recycled to an appropriate area of the process and reused. For example, the raffinate rich in methyl iodide, obtained in the extraction column 92, can be recycled to the distillation column 91 through a line 110. The liquid from the line 113 is usually discharged to the outside as water discharge. A gas that has not been condensed in the condenser 91a or 93a (line 106 or 116) is subjected to absorption treatment in the scrubber system 8 or discarded.

According to the flow of FIG. 2, in the case of treating the aqueous phase in the acetaldehyde separation and removal step, for example, the aqueous phase is fed to the distillation column (first acetaldehyde removal column) 91 through the line 101 and separated by distillation into an overhead stream rich in acetaldehyde (line 102) and a residual liquid stream rich in water (line 103). The overhead stream is condensed in the condenser 91a. A portion of the condensate is refluxed to the column top of the distillation column 91 (line 104), and the remaining portion of the condensate is fed to the extraction column 92 (line 105). The condensate fed to the extraction column 92 is subjected to extraction treatment with water introduced from the line 109. The extract obtained by the extraction treatment is fed to the distillation column (second acetaldehyde removal column) 93 through the line 107 and separated by distillation into an overhead stream rich in acetaldehyde (line 112) and a residual liquid stream rich in water (line 113). Then, the overhead stream rich in acetaldehyde is condensed in the condenser 93a. A portion of the condensate is refluxed to the column top of the distillation column 93 (line 114), and the remaining portion of the condensate is discharged to the outside of the system (line 115). The residual liquid stream rich in water, which is a bottom fraction of the first acetaldehyde removal column 91, a raffinate rich in methyl iodide (line 108) obtained in the extraction column 92, and the residual liquid stream rich in water, which is a bottom fraction of the second acetaldehyde removal column 93 are recycled to the reaction vessel 1 through the lines 103, 111, and 113, respectively, or recycled to an appropriate area of the process and reused. For example, the raffinate rich in methyl iodide, obtained in the extraction column 92, can be recycled to the distillation column 91 through the line 110. The liquid from the line 113 is usually discharged to the outside as water discharge. A gas that has not been condensed in the condenser 91a or 93a (line 106 or 116) is subjected to absorption treatment in the scrubber system 8 or discarded.

The acetaldehyde derived from the process stream containing at least the water, the acetic acid (AC), the methyl iodide (MeI), and the acetaldehyde (AD) can also be separated and removed by use of extractive distillation, in addition to the method described above. For example, the organic phase and/or the aqueous phase (charging mixture) obtained by the separation of the process stream is fed to a distillation column (extractive distillation column). In addition, an extraction solvent (usually, water) is introduced to a concentration zone (e.g., space from the column top to the charging mixture feeding position) where methyl iodide and acetaldehyde in the distillation column are concentrated. A liquid (extract) dropped from the concentration zone is withdrawn as a side stream (side cut stream). This side stream is separated into an aqueous phase and an organic phase. The aqueous phase can be distilled to thereby discharge acetaldehyde to the outside of the system. In the case where a relatively large amount of water is present in the distillation column, the liquid dropped from the concentration zone may be withdrawn as a side stream without introducing the extraction solvent to the distillation column. For example, a unit (chimney tray, etc.) that can receive the liquid (extract) dropped from the concentration zone is disposed in this distillation column so that a liquid (extract) received by this unit can be withdrawn as a side stream. The extraction solvent introduction position is preferably superior to the charging mixture feeding position, more preferably near the column top. The side stream withdrawal position is preferably lower than the extraction solvent introduction position and higher than the charging mixture feeding position, in the height direction of the column. According to this method, acetaldehyde can be extracted with a high concentration from a concentrate of methyl iodide and the acetaldehyde using an extraction solvent (usually, water). In addition, the region between the extraction solvent introduction site and the side cut site is used as an extraction zone. Therefore, acetaldehyde can be efficiently extracted with a small amount of the extraction solvent. Therefore, for example, the number of plates in the distillation column can be drastically decreased as compared with a method of withdrawing an extract by extractive distillation from the column bottom of the distillation column (extractive distillation column). In addition, steam load can also be reduced. Furthermore, the ratio of methyl iodide to acetaldehyde (MeI/AD ratio) in a water extract can be decreased as compared with a method of combining the acetaldehyde removing distillation of FIG. 2 with water extraction using a small amount of an extraction solvent. Therefore, acetaldehyde can be removed under conditions that can suppress a loss of methyl iodide to the outside of the system. The acetaldehyde concentration in the side stream is much higher than the acetaldehyde concentration in the charging mixture and the bottom fraction (column bottom fraction). The ratio of acetaldehyde to methyl iodide in the side stream is larger than the ratio of acetaldehyde to methyl iodide in the charging mixture and the bottom fraction. The organic phase (methyl iodide phase) obtained by the separation of the side stream may be recycled to this distillation column. In this case, the recycle position of the organic phase obtained by the separation of the side stream is preferably lower than the side stream withdrawal position and preferably higher than the charging mixture feeding position, in the height direction of the column. A solvent miscible with the components (e.g., methyl acetate) constituting the organic phase obtained by the separation of the process stream may be introduced to this distillation column (extractive distillation column). Examples of the miscible solvent include acetic acid and ethyl acetate. The miscible solvent introduction position is preferably lower than the side stream withdrawal position and preferably higher than the charging mixture feeding position, in the height direction of the column. Also, the miscible solvent introduction position is preferably inferior to a recycle position in the case where the organic phase obtained by the separation of the side stream is recycled to this distillation column. The organic phase obtained by the separation of the side stream is recycled to the distillation column, or the miscible solvent is introduced to the distillation column, whereby the methyl acetate concentration in the extract withdrawn as the side stream can be decreased, and the methyl acetate concentration in the aqueous phase obtained by the separation of the extract can be lowered. Hence, the contamination of the aqueous phase with methyl iodide can be suppressed.

The theoretical number of plates of the distillation column (extractive distillation column) is, for example, 1 to 100, preferably 2 to 50, further preferably 3 to 30, particularly preferably 5 to 20. Acetaldehyde can be efficiently separated and removed by a smaller number of plates than 80 to 100 plates in a distillation column or an extractive distillation column for use in conventional acetaldehyde removal. The mass ratio between the flow rate of the extraction solvent and the flow rate of the charging mixture (the organic phase and/or the aqueous phase obtained by the separation of the process stream) (former/latter) may be selected from the range of 0.0001/100 to 100/100 and is usually 0.0001/100 to 20/100, preferably 0.001/100 to 10/100, more preferably 0.01/100 to 8/100, further preferably 0.1/100 to 5/100. The column top temperature of the distillation column (extractive distillation column) is, for example, 15 to 120° C., preferably 20 to 90° C., more preferably 20 to 80° C., further preferably 25 to 70° C. The column top pressure is, on the order of, for example, 0.1 to 0.5 MPa in terms of absolute pressure. Other conditions for the distillation column (extractive distillation column) may be the same as those for a distillation column or an extractive distillation column for use in conventional acetaldehyde removal.

FIG. 3 is a schematic flow diagram showing another example of the acetaldehyde separation and removal system using the extractive distillation described above. In this example, the organic phase and/or the aqueous phase (charging mixture) obtained by the separation of the process stream is fed to a middle part (position between the column top and the column bottom) of a distillation column 94 through a feed line 201, while water is introduced thereto from near the column top through a line 202 so that extractive distillation is performed in the distillation column 94 (extractive distillation column). A chimney tray 200 for receiving a liquid (extract) dropped from a concentration zone where methyl iodide and acetaldehyde in the column are concentrated is disposed superior to the charging mixture feeding position of the distillation column 94. In this extractive distillation, preferably the whole amount, of the liquid on the chimney tray 200 is withdrawn, introduced to a decanter 95 through a line 208, and separated. The aqueous phase (containing acetaldehyde) in the decanter 95 is introduced to a cooler 95a through a line 212 and cooled so that methyl iodide dissolved in the aqueous phase is separated into 2 phases in a decanter 96. The aqueous phase in the decanter 96 is fed to a distillation column 97 (acetaldehyde removal column) through a line 216 and distilled. The vapor at the column top is led to a condenser 97a through a line 217 and condensed. A portion of the condensate (mainly, acetaldehyde and methyl iodide) is refluxed to the column top of the distillation column 97, and the remaining portion is discarded or fed to a distillation column 98 (extractive distillation column) through a line 220. Water is introduced thereto from near the column top of the distillation column 98 through a line 222, followed by extractive distillation. The vapor at the column top is led to a condenser 98a through a line 223 and condensed. A portion of the condensate (mainly, methyl iodide) is refluxed to the column top, and the remaining portion is recycled to the reaction system through a line 226, but may be discharged to the outside of the system. Preferably the whole amount, of the organic phase (methyl iodide phase) in the decanter 95 is recycled to below the position of the chimney tray 200 of the distillation column 94 through lines 209 and 210. A portion of the aqueous phase of the decanter 95 and the organic phase of the decanter 96 are recycled to the distillation column 94 through lines 213 and 210 and lines 214 and 210, respectively, but may not be recycled. A portion of the aqueous phase of the decanter 95 may be utilized as an extraction solvent (water) in the distillation column 94. A portion of the aqueous phase of the decanter 96 may be recycled to the distillation column 94 through the line 210. In some cases (e.g., the case where methyl acetate is contained in the charging mixture), a solvent (acetic acid, ethyl acetate, etc.) miscible with the components (e.g., methyl acetate) constituting the organic phase obtained by the separation of the process stream may be fed to the distillation column 94 through a line 215 to thereby improve distillation efficiency. The feeding position of the miscible solvent to the distillation column 94 is superior to the charging mixture feeding portion (junction of the line 201) and inferior to the junction of the recycle line 210. A bottom fraction of the distillation column 94 is recycled to the reaction system. A vapor at the column top of the distillation column 94 is led to a condenser 94*a* through a line 203 and condensed. The condensate is separated in a decanter 99. The organic phase is refluxed to the column top of the distillation column 94 through a line 206, while the aqueous phase is led to the decanter 95 through a line 207. A bottom fraction (water is a main component) of the distillation column 97 and a bottom fraction (water containing a small amount of acetaldehyde) of the distillation column 98 (extractive distillation column) are discharged to the outside of the system through lines 218 and 224, respectively, or recycled to the reaction system. A gas that has not been condensed in the condenser 94*a*, 97*a*, or 98*a* (line 211, 221, or 227) is subjected to absorption treatment in the scrubber system 8, or discarded.

FIG. 4 is a schematic flow diagram showing a further alternative example of the acetaldehyde separation and removal system using the extractive distillation described above. In this example, a condensate of a vapor from the column top of the distillation column 94 is led to a hold tank 100, and the whole amount thereof is refluxed to the column top of the distillation column 94 through the line 206. The other points are the same as in the example of FIG. 3.

FIG. 5 is a schematic flow diagram showing a further alternative example of the acetaldehyde separation and removal system using the extractive distillation described above. In this example, the whole amount of a liquid on the chimney tray 200 is withdrawn, directly introduced to the cooler 95*a* through the line 208 without the medium of the decanter 95, cooled, and fed to the decanter 96. The other points are the same as in the example of FIG. 4.

In FIG. 1 described above, the gaseous portion generated in the condenser 3*a* contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 3*a* through the lines 32 and 15. For example, methyl iodide, hydrogen iodide, water, methyl acetate, acetic acid, dimethyl ether, methanol, acetaldehyde, and formic acid in the gaseous portion that has entered the scrubber system 8 are absorbed to an absorbing liquid in the scrubber system 8. The hydrogen iodide generates methyl iodide through reaction with methanol or methyl acetate in the absorbing liquid. Then, a liquid portion containing useful components such as the methyl iodide is recycled to the reaction vessel 1 from the scrubber system 8 through the recycle lines 48 and 23 and reused.

The bottom fraction withdrawn from the column bottom of the distillation column 3 contains a larger amount of components having a higher boiling point (higher boiling point components) than that of acetic acid as compared with the overhead stream and the side stream from the distillation column 3 and contains, for example, propionic acid, and the entrained catalyst and co-catalyst mentioned above. This bottom fraction also contains, for example, acetic acid, methyl iodide, methyl acetate, and water. In the present embodiment, a portion of such a bottom fraction is continuously introduced to the evaporator 2 through the lines 25 and 26 and recycled, and another portion of the bottom fraction is continuously introduced to the reaction vessel 1 through the lines 25 and 23 and recycled.

The first acetic acid stream continuously withdrawn as a side stream from the distillation column 3 is more enriched with acetic acid than the vapor stream continuously introduced to the distillation column 3. Specifically, the acetic acid concentration of the first acetic acid stream is higher than the acetic acid concentration of the vapor stream. The acetic acid concentration of the first acetic acid stream is, for example, 90 to 99.9% by mass, preferably 93 to 99% by mass. Also, the first acetic acid stream may contain, in addition to acetic acid, for example, methyl iodide, hydrogen iodide, water, methyl acetate, dimethyl ether, methanol, acetaldehyde, formic acid, and propionic acid. The first acetic acid stream has a methyl iodide concentration of, for example, not more than 8% by mass (e.g., 0.1 to 8% by mass), preferably 0.2 to 5% by mass, a water concentration of, for example, not more than 8% by mass (e.g., 0.1 to 8% by mass), preferably 0.2 to 5% by mass, and a methyl acetate concentration of, for example, not more than 8% by mass (e.g., 0.1 to 8% by mass), preferably 0.2 to 5% by mass. The connection position of the line 27 to the distillation column 3 may be, as shown in the drawing, higher than the connection position of the line 21 to the distillation column 3 in the height direction of the distillation column 3, but may be lower than the connection position of the line 21 to the distillation column 3 or may be the same as the connection position of the line 21 to the distillation column 3. The first acetic acid stream from the distillation column 3 is continuously introduced at a predetermined flow rate to the next distillation column 5 through the line 27. The first acetic acid stream withdrawn as a side stream from the distillation column 3, column bottom fraction of the distillation column 3, or condensate of the vapor in the column bottom of the distillation column 3 may be directly used as product acetic acid, or may be directly introduced into the distillation column 6 without using the distillation column 5.

To the first acetic acid stream flowing through the line 27, potassium hydroxide can be fed or added through the line 55 (potassium hydroxide introduction line). The potassium hydroxide can be fed or added, for example, as a solution such as an aqueous solution. Hydrogen iodide in the first acetic acid stream can be decreased by the feed or addition of potassium hydroxide to the first acetic acid stream. Specifically, the hydrogen iodide reacts with the potassium hydroxide to form potassium iodide and water. This can reduce the corrosion of an apparatus such as a distillation column ascribable to hydrogen iodide. In this process, the potassium hydroxide can be fed or added to an appropriate site where hydrogen iodide is present. The potassium hydroxide added during the process also reacts with acetic acid to form potassium acetate.

The distillation column 5 is a unit for performing the second distillation step and serves as the so-called dehydration column in the present embodiment. The second distillation step is a step for further purifying acetic acid by the distillation treatment of the first acetic acid stream continuously introduced to the distillation column 5. The distillation column 5 consists of, for example, a distillation column such as a plate column or a packed column. In the case of adopting a plate column as the distillation column 5, the theoretical number of plates thereof is, for example, 5 to 50, and the reflux ratio is, for example, 0.2 to 3000 according to the theoretical number of plates. In the inside of the distillation column 5 in the second distillation step, the column top pressure is set to, for example, 150 to 250 kPa (gauge pressure), and the column bottom pressure is higher than the column top pressure and is set to, for example, 160 to 290 kPa (gauge pressure). In the inside of the distillation column 5 in the second distillation step, the column top temperature is, for example, a temperature of higher than the boiling point of water and lower than the boiling point of acetic acid at the set column top pressure and is set to 130 to 160° C., and the column bottom temperature is, for example, a temperature of not less than the boiling point of acetic acid at the set column bottom pressure and is set to 150 to 175° C.

A vapor as an overhead stream is continuously withdrawn to the line 33 from the column top of the distillation column 5. A bottom fraction is continuously withdrawn to the line 34 from the column bottom of the distillation column 5. 5b denotes a reboiler. A side stream (liquid or gas) may be continuously withdrawn to the line 34 from the height position between the column top and the column bottom of the distillation column 5.

The vapor withdrawn from the column top of the distillation column 5 contains a larger amount of components having a lower boiling point (lower boiling point components) than that of acetic acid as compared with the bottom fraction from the distillation column 5 and contains, for example, methyl iodide, hydrogen iodide, water, methyl acetate, acetic acid, dimethyl ether, methanol, acetaldehyde, and formic acid. Such a vapor is continuously introduced to the condenser 5a through the line 33.

The condenser 5a separates the vapor from the distillation column 5 into a condensate portion and a gaseous portion by cooling and partial condensation. The condensate portion contains, for example, water and acetic acid. A portion of the condensate portion is continuously refluxed to the distillation column 5 from the condenser 5a through the line 35. Another portion of the condensate portion is continuously introduced to the reaction vessel 1 from the condenser 5a through the lines 35, 36, and 23 and recycled. The gaseous portion generated in the condenser 5a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 5a through the lines 37 and 15. Hydrogen iodide in the gaseous portion that has entered the scrubber system 8 is absorbed to an absorbing liquid in the scrubber system 8. Methyl iodide is generated through the reaction of the hydrogen iodide with methanol or methyl acetate in the absorbing liquid. Then, a liquid portion containing useful components such as the methyl iodide is recycled to the reaction vessel 1 from the scrubber system 8 through the recycle lines 48 and 23 and reused.

The bottom fraction (or the side stream) withdrawn from the column bottom of the distillation column 5 contains a larger amount of components having a higher boiling point (higher boiling point components) than that of acetic acid as compared with the overhead stream from the distillation column 5 and contains, for example, propionic acid, potassium acetate (in the case of feeding potassium hydroxide to the line 27, etc.), and the entrained catalyst and co-catalyst mentioned above. This bottom fraction may also contain acetic acid. Such a bottom fraction is continuously introduced in the form of the second acetic acid stream to the next distillation column 6 through the line 34.

The second acetic acid stream is more enriched with acetic acid than the first acetic acid stream continuously introduced to the distillation column 5. Specifically, the acetic acid concentration of the second acetic acid stream is higher than the acetic acid concentration of the first acetic acid stream. The acetic acid concentration of the second acetic acid stream is, for example, 99.1 to 99.99% by mass as long as being higher than the acetic acid concentration of the first acetic acid stream. Also, the second acetic acid stream may contain, as described above, in addition to acetic acid, for example, propionic acid and hydrogen iodide. In the present embodiment, in the case of withdrawing a side stream, the withdrawal position of the side stream from the distillation column 5 is lower than the introduction position of the first acetic acid stream to the distillation column 5 in the height direction of the distillation column 5.

To the second acetic acid stream flowing through the line 34, potassium hydroxide can be fed or added through the line 56 (potassium hydroxide introduction line). The potassium hydroxide can be fed or added, for example, as a solution such as an aqueous solution. Hydrogen iodide in the second acetic acid stream can be decreased by the feed or addition of potassium hydroxide to the second acetic acid stream. Specifically, the hydrogen iodide reacts with the potassium hydroxide to form potassium iodide and water. This can reduce the corrosion of an apparatus such as a distillation column ascribable to hydrogen iodide.

The distillation column 6 is a unit for performing the third distillation step and serves as the so-called higher boiling point component removal column in the present embodiment. The third distillation step is a step for further purifying acetic acid by the purification treatment of the second acetic acid stream continuously introduced to the distillation column 6. The distillation column 6 consists of, for example, a distillation column such as a plate column or a packed column. In the case of adopting a plate column as the distillation column 6, the theoretical number of plates thereof is, for example, 5 to 50, and the reflux ratio is, for example, 0.2 to 3000 according to the theoretical number of plates. In the inside of the distillation column 6 in the third distillation step, the column top pressure is set to, for example, −100 to 150 kPa (gauge pressure), and the column bottom pressure is higher than the column top pressure and is set to, for example, −90 to 180 kPa (gauge pressure). In the inside of the distillation column 6 in the third distillation step, the column top temperature is, for example, a temperature of higher than the boiling point of water and lower than the boiling point of acetic acid at the set column top pressure and is set to 50 to 150° C., and the column bottom temperature is, for example, a temperature of higher than the boiling point of acetic acid at the set column bottom pressure and is set to 70 to 160° C.

A vapor as an overhead stream is continuously withdrawn to the line 38 from the column top of the distillation column 6. A bottom fraction is continuously withdrawn to the line 39 from the column bottom of the distillation column 6. 6b denotes a reboiler. A side stream (liquid or gas) is continuously withdrawn to the line 46 from the height position between the column top and the column bottom of the distillation column 6. The connection position of the line 46 to the distillation column 6 may be, as shown in the drawing, higher than the connection position of the line 34 to the distillation column 6 in the height direction of the distillation column 6, but may be lower than the connection position of the line 34 to the distillation column 6 or may be the same as the connection position of the line 34 to the distillation column 6.

The vapor withdrawn from the column top of the distillation column 6 contains a larger amount of components having a lower boiling point (lower boiling point components) than that of acetic acid as compared with the bottom fraction from the distillation column 6 and contains, in addition to acetic acid, for example, methyl iodide, hydrogen iodide, water, methyl acetate, dimethyl ether, methanol, and formic acid. Such a vapor is continuously introduced to the condenser 6a through the line 38.

The condenser 6a separates the vapor from the distillation column 6 into a condensate portion and a gaseous portion by cooling and partial condensation. The condensate portion contains, in addition to acetic acid, for example, methyl iodide, hydrogen iodide, water, methyl acetate, dimethyl ether, methanol, and formic acid. At least a portion of the condensate portion is continuously refluxed to the distillation column 6 from the condenser 6a through the line 40. A portion (distillate) of the condensate portion may be recycled to the first acetic acid stream in the line 27 before introduction to the distillation column 5 from the condenser 6a through the lines 40, 41, and 42. Together with this or instead of this, a portion (distillate) of the condensate portion may be recycled to the vapor stream in the line 21 before introduction to the distillation column 3 from the condenser 6a through the lines 40, 41, and 43. Also, a portion (distillate) of the condensate portion may be recycled to the reaction vessel 1 from the condenser 6a through the lines 40, 44, and 23. Furthermore, as mentioned above, a portion of the distillate from the condenser 6a may be fed to the scrubber system 8 and used as an absorbing liquid in this system. In the scrubber system 8, a gaseous portion after absorption of a useful portion is discharged to the outside of the apparatus. Then, a liquid portion containing the useful components is introduced or recycled to the reaction vessel 1 from the scrubber system 8 through the recycle lines 48 and 23 and reused. In addition, a portion of the distillate from the condenser 6a may be led to various pumps (not shown) operated in the apparatus, through lines (not shown) and used as sealing solutions in these pumps. In addition, a portion of the distillate from the condenser 6a may be steadily withdrawn to the outside of the apparatus through a withdrawal line attached to the line 40, or may be non-steadily withdrawn to the outside of the apparatus when needed. In the case where a portion (distillate) of the condensate portion is removed from the distillation treatment system in the distillation column 6, the amount of the distillate (ratio of the distillate) is, for example, 0.01 to 30% by mass, preferably 0.1 to 10% by mass, more preferably 0.3 to 5% by mass, more preferably 0.5 to 3% by mass, of the condensate generated in the condenser 6a. On the other hand, the gaseous portion generated in the condenser 6a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 6a through the lines 45 and 15.

The bottom fraction withdrawn from the column bottom of the distillation column 6 through the line 39 contains a larger amount of components having a higher boiling point (higher boiling point components) than that of acetic acid as compared with the overhead stream from the distillation column 6 and contains, for example, propionic acid and potassium acetate (in the case of feeding potassium hydroxide to the line 34, etc.). Also, the bottom fraction withdrawn from the column bottom of the distillation column 6 through the line 39 also contains, for example, a corroded metal such as a metal formed at and released from the inside wall of a member constituting this acetic acid production apparatus, and a compound of iodine derived from corrosive iodine and the corroded metal, etc. In the present embodiment, such a bottom fraction is discharged to the outside of the acetic acid production apparatus.

The side stream continuously withdrawn to the line 46 from the distillation column 6 is continuously introduced as a third acetic acid stream to the next ion exchange resin column 7. This third acetic acid stream is more enriched with acetic acid than the second acetic acid stream continuously introduced to the distillation column 6. Specifically, the acetic acid concentration of the third acetic acid stream is higher than the acetic acid concentration of the second acetic acid stream. The acetic acid concentration of the third acetic acid stream is, for example, 99.8 to 99.999% by mass as long as being higher than the acetic acid concentration of the second acetic acid stream. In the present embodiment, the withdrawal position of the side stream from the distillation column 6 is higher than the introduction position of the second acetic acid stream to the distillation column 6 in the height direction of the distillation column 6. In another embodiment, the withdrawal position of the side stream from the distillation column 6 is the same as or lower than the introduction position of the second acetic acid stream to the distillation column 6 in the height direction of the distillation column 6. A simple distillator (evaporator) may be used in place of the distillation column 6. Also, the distillation column 6 can be omitted as long as the removal of impurities in the distillation column 5 is adequately performed.

The ion exchange resin column 7 is a purification unit for performing the adsorptive removal step. This adsorptive removal step is a step for further purifying acetic acid by the adsorptive removal of, mainly, alkyl iodides (hexyl iodide, decyl iodide, etc.) contained in a very small amount in the third acetic acid stream continuously introduced to the ion exchange resin column 7. In the ion exchange resin column 7, an ion exchange resin having the ability to adsorb alkyl iodides is packed in the column to establish an ion exchange resin bed. Examples of such an ion exchange resin can include cation exchange resins in which a portion of leaving protons in an exchange group such as a sulfonic acid group, a carboxyl group, or a phosphonic acid group is substituted by a metal such as silver or copper. In the adsorptive removal step, for example, the third acetic acid stream (liquid) flows through the inside of the ion exchange resin column 7 packed with such an ion exchange resin, and in the course of this flow, impurities such as the alkyl iodides in the third acetic acid stream are adsorbed to the ion exchange resin and removed from the third acetic acid stream. In the ion exchange resin column 7 in the adsorptive removal step, the internal temperature is, for example, 18 to 100° C., and the rate of the acetic acid stream [the throughput of acetic acid per m$^3$ resin volume (m$^3$/h)] is, for example, 3 to 15 m$^3$/h·m$^3$ (resin volume).

A fourth acetic acid stream is continuously led to the line 47 from the lower end of the ion exchange resin column 7. The acetic acid concentration of the fourth acetic acid stream is higher than the acetic acid concentration of the third acetic acid stream. Specifically, the fourth acetic acid stream is more enriched with acetic acid than the third acetic acid stream continuously introduced to the ion exchange resin column 7. The acetic acid concentration of the fourth acetic acid stream is, for example, 99.9 to 99.999% by mass or not less than this range as long as being higher than the acetic acid concentration of the third acetic acid stream. In this production method, this fourth acetic acid stream can be retained in a product tank (not shown).

In this acetic acid production apparatus, a so-called product column or finishing column which is a distillation column may be disposed as a purification unit for further purifying the fourth acetic acid stream from the ion exchange resin column 7. In the case where such a product column is disposed, the product column consists of, for example, a distillation column such as a plate column or a packed column. In the case of adopting a plate column as the product column, the theoretical number of plates thereof is, for example, 5 to 50, and the reflux ratio is, for example, 0.5 to 3000 according to the theoretical number of plates. In the inside of the product column in the purification step, the column top pressure is set to, for example, −195 to 150 kPa (gauge pressure), and the column bottom pressure is higher than the column top pressure and is set to, for example, −190 to 180 kPa (gauge pressure). In the inside of the product column, the column top temperature is, for example, a temperature of higher than the boiling point of water and lower than the boiling point of acetic acid at the set column top pressure and is set to 50 to 150° C., and the column bottom temperature is, for example, a temperature of higher than the boiling point of acetic acid at the set column bottom pressure and is set to 70 to 160° C. A simple distillator (evaporator) may be used in place of the product column or the finishing column.

In the case of disposing the product column, the whole or a portion of the fourth acetic acid stream (liquid) from the ion exchange resin column 7 is continuously introduced to the product column. A vapor as an overhead stream containing a very small amount of lower boiling point components (e.g., methyl iodide, water, methyl acetate, dimethyl ether, crotonaldehyde, acetaldehyde, and formic acid) is continuously withdrawn from the column top of such a product column. This vapor is separated into a condensate portion and a gaseous portion in a predetermined condenser. A portion of the condensate portion is continuously refluxed to the product column, and another portion of the condensate portion may be recycled to the reaction vessel 1 or discarded to the outside of the system, or both. The gaseous portion is fed to the scrubber system 8. A bottom fraction containing a very small amount of higher boiling point components is continuously withdrawn from the column bottom of the product column. This bottom fraction is recycled to, for example, the second acetic acid stream in the line 34 before introduction to the distillation column 6. A side stream (liquid) is continuously withdrawn as a fifth acetic acid stream from the height position between the column top and the column bottom of the product column. The withdrawal position of the side stream from the product column is lower than, for example, the introduction position of the fourth acetic acid stream to the product column in the height direction of the product column. The fifth acetic acid stream is more enriched with acetic acid than the fourth acetic acid stream continuously introduced to the product column. Specifically, the acetic acid concentration of the fifth acetic acid stream is higher than the acetic acid concentration of the fourth acetic acid stream. The acetic acid concentration of the fifth acetic acid stream is, for example, 99.9 to 99.999% by mass or not less than this range as long as being higher than the acetic acid concentration of the fourth acetic acid stream. This fifth acetic acid stream is retained in, for example, a product tank (not shown). The ion exchange resin column 7 may be placed downstream of the product column instead of (or in addition to) its placement downstream of the distillation column 6 to treat the acetic acid stream from the product column.

EXAMPLES

Hereinafter, the present invention will be described in more detail with reference to Examples. However, the present invention is not intended to be limited by these Examples. "AD" represents acetaldehyde, "MeI" represents methyl iodide, "MA" represents methyl acetate, and "AC" represents acetic acid. The measurements of each component concentration in an aqueous phase and an organic phase were performed by using gas chromatography for the components except for water and using a Karl Fischer water determination apparatus for water. The AD distribution coefficient between the aqueous phase and the organic phase, and the MA distribution coefficient between the aqueous phase and the organic phase were determined according to the following expressions:

AD distribution coefficient={AD concentration (% by mass) of the aqueous phase}/{AD concentration (% by mass) of the organic phase}

MA distribution coefficient={MA concentration (% by mass) of the aqueous phase}/{MA concentration (% by mass) of the organic phase}

Examples 1 to 10

Examples 1 to 10 employed a liquid-liquid equilibrium measurement apparatus 300 adaptable to a pressurized system shown in FIG. 6, and experiments were conducted to examine each component concentration in an aqueous phase and an organic phase and an AD distribution coefficient by changing an AD concentration in a charging mixture to be subjected to the separation step (separation step feeding liquid). In FIG. 6, 301 denotes a pressure-resistant glass container (internal volume: 100 cc), 302 denotes a stirrer chip (rugby ball-shaped), 303 denotes a lower phase withdrawal tube, 304 denotes an upper phase withdrawal tube, 305 denotes a thermometer, 306 denotes a magnet stirrer, 307 denotes a water bath, 308 denotes a temperature controller, 309 denotes a thermometer, 310 denotes a lower phase sampling tube, 311 denotes an upper phase sampling tube, 312 denotes a pressure gauge, 313 denotes a pressure regulating valve, 314, 315, 316, and 317 each denote a valve, 318 denotes a safety valve, 319 denotes a lower phase withdrawal line, 320 denotes an upper phase withdrawal line, 321 denotes a nitrogen gas introduction line, 322 denotes a pressure discharge line, and 323 denotes an exhaust line. The dotted line represents a liquid level or an interface.

AD, MeI, and water were fed in amounts shown in the column "Actual feed amount" of Table 1 to the pressure-resistant glass container 301. The stirrer chip 302 was placed therein, and the container was covered with a lid. After purging of the inside with nitrogen, the temperature was adjusted as shown in the column "Temperature" of Table 1 using the water bath 307, followed by stirring at 300 rpm for 30 minutes. After stopping of the stirring, the container was left for 10 minutes for complete separation. Then, the aqueous phase and the organic phase (methyl iodide phase) were sampled into the sampling tubes 311 and 310, respectively, and their respective AD, MeI, and water concentrations were measured, while the AD distribution coefficient was determined. The results are shown in Table 1.

Examples 11 to 15

In Examples 11 to 15, experiments were conducted to examine each component concentration in an aqueous phase and an organic phase and an AD distribution coefficient when an AD concentration in a charging mixture was kept constant and a temperature (liquid temperature) in the separation step was changed.

The amounts of AD, MeI, and water fed to the pressure-resistant glass container 301 and the temperature were set to the values shown in Table 1. The experiments according to the same procedures as in Examples 1 to 10 were performed to measure each component concentration in the aqueous phase and the organic phase and to determine the AD distribution coefficient. The results are shown in Table 1.

Examples 16 to 21

In Examples 16 to 21, experiments were conducted to examine each component concentration in an aqueous phase and an organic phase, an AD distribution coefficient, and a MA distribution coefficient when an AD concentration and a MA concentration in a charging mixture were kept constant and a temperature (liquid temperature) in the separation step was changed.

The amounts of AD, MeI, MA, and water fed to the pressure-resistant glass container 301 and the temperature were set to the values shown in Table 2. The experiments according to the same procedures as in Examples 1 to 10 were performed to measure each component concentration in the aqueous phase and the organic phase and to determine the AD distribution coefficient and the MA distribution coefficient. The results are shown in Table 2.

Examples 22 to 26

In Examples 22 to 26, experiments were conducted to examine each component concentration in an aqueous phase and an organic phase and an AD distribution coefficient and an MA distribution coefficient by changing an MA concentration in a charging mixture.

The amounts of AD, MeI, MA, and water fed to the pressure-resistant glass container 301 and the temperature were set to the values shown in Table 2. The experiments according to the same procedures as in Examples 1 to 10 were performed to measure each component concentration in the aqueous phase and the organic phase and to determine the AD distribution coefficient and the MA distribution coefficient. The results are shown in Table 2.

Reference Examples 1 and 2

In Reference Examples 1 and 2, experiments were conducted to examine each component concentration in an aqueous phase and an organic phase and an AD distribution coefficient by changing an AC concentration in a charging mixture.

The amounts of AD, MeI, water, and AC fed to the pressure-resistant glass container 301 and the temperature were set to the values shown in Table 2. The experiments according to the same procedures as in Examples 1 to 10 were performed to measure each component concentration in the aqueous phase and the organic phase and to determine the AD distribution coefficient. The results are shown in Table 2.

TABLE 1

| Example | | Example 1 | Example 2 | Example 3 | Example 4 | Example 5 | Example 6 | Example 7 | Example 8 |
|---|---|---|---|---|---|---|---|---|---|
| Actual feed amount [g] | AD | 0.05 | 0.11 | 0.20 | 0.39 | 0.81 | 1.62 | 5.63 | 21.20 |
| | MeI | 132.15 | 132.02 | 132.10 | 132.95 | 131.91 | 132.05 | 128.04 | 115.06 |
| | MA | | | | | | | | |
| | H2O | 60.09 | 60.09 | 60.11 | 60.23 | 59.85 | 60.15 | 54.01 | 41.05 |
| | AC | | | | | | | | |
| | total | 192.29 | 192.22 | 192.41 | 193.57 | 192.57 | 193.82 | 187.68 | 177.31 |
| Temperature | [° C.] | 40 | 40.2 | 40.1 | 40.2 | 40.2 | 40.2 | 40.1 | 40.1 |
| Pressure | [MPaG] | 0.05 | 0.05 | 0.05 | 0.05 | 0.05 | 0.05 | 0.05 | 0.07 |
| Actual feed [wt %] | AD | 0.026% | 0.057% | 0.104% | 0.201% | 0.42% | 0.84% | 3.0% | 12.0% |
| | MeI | 68.7% | 68.7% | 68.7% | 68.7% | 68.5% | 68.1% | 68.2% | 64.9% |
| | MA | | | | | | | | |
| | H2O | 31.2% | 31.3% | 31.2% | 31.1% | 31.1% | 31.0% | 28.8% | 23.2% |
| | AC | | | | | | | | |
| | total | 100.0% | 100.0% | 100.0% | 100.0% | 100.0% | 100.0% | 100.0% | 100.0% |
| Aqueous phase [wt %] | AD | 0.045% | 0.098% | 0.190% | 0.371% | 0.76% | 1.539% | 5.22% | 16.78% |
| | MeI | 2.45% | 2.45% | 2.45% | 2.46% | 2.47% | 2.49% | 2.53% | 3.09% |
| | MA | | | | | | | | |
| | H2O | 97.50% | 97.45% | 97.36% | 97.17% | 96.77% | 95.97% | 92.24% | 80.14% |
| | AC | | | | | | | | |
| | total | 100.0% | 100.0% | 100.0% | 100.0% | 100.0% | 100.0% | 100.0% | 100.0% |
| Organic phase [wt %] | AD | 0.013% | 0.030% | 0.058% | 0.115% | 0.240% | 0.495% | 1.95% | 9.48% |
| | MeI | 99.49% | 99.47% | 99.44% | 99.39% | 99.26% | 99.01% | 97.18% | 90.06% |
| | MA | | | | | | | | |
| | H2O | 0.50% | 0.50% | 0.50% | 0.50% | 0.50% | 0.50% | 0.87% | 0.46% |
| | AC | | | | | | | | |
| | total | 100.0% | 100.0% | 100.0% | 100.0% | 100.0% | 100.0% | 100.0% | 100.0% |
| AD distribution coefficient (aqueous phase/organic phase) | | 3.35 | 3.30 | 3.26 | 3.22 | 3.17 | 3.11 | 2.68 | 1.8 |

TABLE 1-continued

| Example | | Example 9 | Example 10 | Example 11 | Example 12 | Example 13 | Example 14 | Example 15 |
|---|---|---|---|---|---|---|---|---|
| Actual feed amount [g] | AD | 24.80 | 35.21 | 0.41 | 0.39 | 0.41 | 0.39 | 0.42 |
| | MeI | 101.12 | 66.04 | 104.03 | 104.03 | 111.33 | 112.87 | 114.12 |
| | MA | | | | | | | |
| | H2O | 29.01 | 33.99 | 37.00 | 37.00 | 39.42 | 39.90 | 40.41 |
| | AC | | | | | | | |
| | total | 154.93 | 135.24 | 141.44 | 141.42 | 151.16 | 153.16 | 154.95 |
| Temperature [° C.] | | 40.2 | 40.2 | 70.0 | 50.0 | 30.6 | 20.6 | 11.1 |
| Pressure [MPaG] | | 0.08 | 0.10 | 0.13 | 0.13 | 0.07 | 0.03 | 0.01 |
| Actual feed [wt %] | AD | 16.0% | 26.0% | 0.3% | 0.3% | 0.3% | 0.3% | 0.3% |
| | MeI | 65.3% | 48.8% | 73.6% | 73.6% | 73.7% | 73.7% | 73.6% |
| | MA | | | | | | | |
| | H2O | 18.7% | 25.1% | 26.2% | 26.2% | 26.1% | 26.1% | 26.1% |
| | AC | | | | | | | |
| | total | 100.0% | 100.0% | 100.0% | 100.0% | 100.0% | 100.0% | 100.0% |
| Aqueous phase [wt %] | AD | 20.64% | 28.10% | 0.44% | 0.51% | 0.54% | 0.50% | 0.60% |
| | MeI | 3.98% | 5.43% | 2.47% | 2.46% | 3.37% | 2.40% | 2.30% |
| | MA | | | | | | | |
| | H2O | 75.37% | 66.47% | 97.09% | 97.03% | 96.09% | 97.10% | 97.10% |
| | AC | | | | | | | |
| | total | 100.0% | 100.0% | 100.0% | 100.0% | 100.0% | 100.0% | 100.0% |
| Organic phase [wt %] | AD | 14.06% | 24.80% | 0.230% | 0.181% | 0.153% | 0.122% | 0.143% |
| | MeI | 85.18% | 73.34% | 99.13% | 99.18% | 99.45% | 99.56% | 99.57% |
| | MA | | | | | | | |
| | H2O | 0.77% | 1.86% | 0.64% | 0.64% | 0.40% | 0.32% | 0.28% |
| | AC | | | | | | | |
| | total | 100.0% | 100.0% | 100.0% | 100.0% | 100.0% | 100.0% | 100.0% |
| AD distribution coefficient (aqueous phase/organic phase) | | 1.5 | 1.1 | 1.9 | 2.8 | 3.5 | 4.1 | 4.2 |

TABLE 2

| Example | | Example 16 | Example 17 | Example 18 | Example 19 | Example 20 | Example 21 | Example 22 | Example 23 | Example 24 | Example 25 | Example 26 | Reference Example 1 | Reference Example 2 |
|---|---|---|---|---|---|---|---|---|---|---|---|---|---|---|
| Actual feed amount [g] | AD | 0.40 | 0.41 | 0.41 | 0.39 | 0.40 | 0.44 | 0.42 | 0.40 | 0.43 | 0.42 | 0.42 | 0.41 | 0.40 |
| | MeI | 88.49 | 89.68 | 94.94 | 98.18 | 101.08 | 105.53 | 127.09 | 109.12 | 78.01 | 46.03 | 46.03 | 113.01 | 92.02 |
| | MA | 7.43 | 7.55 | 7.98 | 8.21 | 8.55 | 8.43 | 3.80 | 8.68 | 23.03 | 39.03 | 56.00 | | |
| | H2O | 34.21 | 34.66 | 36.72 | 37.59 | 39.01 | 40.50 | 59.01 | 55.97 | 50.01 | 44.02 | 44.02 | 58.00 | 57.00 |
| | AC | | | | | | | | | | | | 9.01 | 17.02 |
| | total | 130.53 | 132.30 | 140.05 | 144.37 | 149.04 | 154.90 | 190.32 | 174.17 | 151.48 | 129.50 | 146.47 | 180.43 | 166.44 |
| Temperature [° C.] | | 50.3 | 40.6 | 30.5 | 21.0 | 11.3 | −5.1 | 40.3 | 40.3 | 40.3 | 40.5 | 40.5 | 40.0 | 40.0 |
| Pressure [MPaG] | | 0.14 | 0.11 | 0.07 | 0.05 | 0.02 | 0.02 | 0.06 | 0.06 | 0.06 | 0.06 | 0.06 | 0.06 | 0.06 |
| Actual feed [wt %] | AD | 0.31% | 0.31% | 0.29% | 0.27% | 0.27% | 0.28% | 0.22% | 0.23% | 0.28% | 0.32% | 0.29% | 0.23% | 0.24% |
| | MeI | 67.8% | 67.8% | 67.8% | 68.0% | 67.8% | 68.1% | 66.8% | 62.7% | 51.5% | 35.5% | 31.4% | 62.6% | 55.3% |
| | MA | 5.7% | 5.7% | 5.7% | 5.7% | 5.7% | 5.4% | 2.0% | 5.0% | 15.2% | 30.1% | 38.2% | | |
| | H2O | 26.2% | 26.2% | 26.2% | 26.0% | 26.2% | 26.1% | 31.0% | 32.1% | 33.0% | 34.0% | 30.1% | 32.1% | 34.2% |
| | AC | | | | | | | | | | | | 5.0% | 10.2% |
| | total | 100.0% | 100.0% | 100.0% | 100.0% | 100.0% | 100.0% | 100.0% | 100.0% | 100.0% | 100.0% | 100.0% | 100.0% | 100.0% |
| Aqueous phase [wt %] | AD | 0.55% | 0.60% | 0.61% | 0.55% | 0.54% | 0.56% | 0.46% | 0.42% | 0.41% | 0.37% | 0.30% | 0.40% | 0.39% |
| | MeI | 3.72% | 2.83% | 2.62% | 2.58% | 2.97% | 2.88% | 2.31% | 2.23% | 1.68% | 1.45% | 1.20% | 3.09% | 3.37% |
| | MA | 2.28% | 2.18% | 2.25% | 2.30% | 2.48% | 2.51% | 1.21% | 2.56% | 6.01% | 10.36% | 12.00% | | |
| | H2O | 93.45% | 94.40% | 94.53% | 94.57% | 94.01% | 94.05% | 96.03% | 94.79% | 91.90% | 87.82% | 86.50% | 84.90% | 73.89% |
| | AC | | | | | | | | | | | | 11.61% | 22.35% |
| | total | 100.0% | 100.0% | 100.0% | 100.0% | 100.0% | 100.0% | 100.0% | 100.0% | 100.0% | 100.0% | 100.0% | 100.0% | 100.0% |

TABLE 2-continued

| Example | | Example 16 | Example 17 | Example 18 | Example 19 | Example 20 | Example 21 | Example 22 | Example 23 | Example 24 | Example 25 | Example 26 | Reference Example 1 | Reference Example 2 |
|---|---|---|---|---|---|---|---|---|---|---|---|---|---|---|
| Organic phase [wt %] | AD | 0.190% | 0.194% | 0.179% | 0.145% | 0.132% | 0.124% | 0.134% | 0.136% | 0.21% | 0.29% | 0.28% | 0.127% | 0.125% |
| | MeI | 93.00% | 93.16% | 93.25% | 93.45% | 93.47% | 93.60% | 95.71% | 93.50% | 79.34% | 56.63% | 49.15% | 98.88% | 98.75% |
| | MA | 5.94% | 5.92% | 5.96% | 5.92% | 5.99% | 5.90% | 2.29% | 5.81% | 19.57% | 41.08% | 47.57% | | |
| | H2O | 0.87% | 0.73% | 0.60% | 0.48% | 0.42% | 0.38% | 1.87% | 0.55% | 0.88% | 2.00% | 3.00% | 0.24% | 0.28% |
| | AC | | | | | | | | | | | | 0.75% | 0.85% |
| | total | 100.0% | 100.0% | 100.0% | 100.0% | 100.0% | 100.0% | 100.0% | 100.0% | 100.0% | 100.0% | 100.0% | 100.0% | 100.0% |
| AD distribution coefficient (aqueous phase/organic phase) | | 2.9 | 3.1 | 3.4 | 3.8 | 4.1 | 4.5 | 3.4 | 3.1 | 1.9 | 1.3 | 1.1 | 3.1 | 3.1 |
| Aqueous phase MA concentration + organic phase MA concentration [wt %] | | 8.22% | 8.01% | 8.21% | 8.22% | 8.47% | 8.41% | 3.50% | 8.37% | 25.58% | 51.44% | 59.57% | | |
| MA distribution coefficient (aqueous phase/organic phase) | | 0.38 | 0.37 | 0.38 | 0.39 | 0.41 | 0.43 | 0.53 | 0.44 | 0.31 | 0.25 | 0.25 | | |

[Discussion on Results]

From the results of Examples 1 to 10, it is evident that as the charging mixture has a higher AD concentration and the aqueous phase and the organic phase have higher AD concentrations, the AD distribution coefficient is smaller so that the rate of distribution of AD to the organic phase tends to be relatively higher. Specifically, from the viewpoint of acetaldehyde removal efficiency, the AD removal treatment of the organic phase is highly advantageous in the case where the AD concentrations in the aqueous phase and the organic phase are high, whereas the AD removal treatment of the organic phase is low advantageous in the case where the AD concentrations in the aqueous phase and the organic phase are low. On the other hand, the AD removal treatment of the aqueous phase is highly advantageous in the case where the AD concentrations in the aqueous phase and the organic phase are low, whereas the AD removal treatment of the aqueous phase is low advantageous in the case where the AD concentrations in the aqueous phase and the organic phase are high. From another viewpoint, in the case of using a step or equipment for the AD removal treatment of the organic phase, it is preferred to increase the AD concentration in the aqueous phase and/or the organic phase in the separation step by adjusting, for example, reaction conditions for a reaction vessel, evaporation conditions for an evaporator, and distillation conditions for a vapor stream obtained in the evaporation step. Also, in the case of using a step or equipment for the AD removal treatment of the aqueous phase, it is preferred to decrease the AD concentrations in the aqueous phase and/or the organic phase in the separation step by adjusting, for example, reaction conditions for a reaction vessel, evaporation conditions for an evaporator, and distillation conditions for a vapor stream obtained in the evaporation step.

From the results of Examples 11 to 15, it is evident that under the constant AD concentration condition, at a higher temperature at the time of the separation, the AD distribution coefficient is smaller so that the rate of distribution of AD to the organic phase tends to be relatively higher. Specifically, from the viewpoint of acetaldehyde removal efficiency, the AD removal treatment of the organic phase is highly advantageous in the case where the temperature at the time of the separation is high, whereas the AD removal treatment of the organic phase is low advantageous in the case where the temperature at the time of the separation is low. On the other hand, the AD removal treatment of the aqueous phase is highly advantageous in the case where the temperature at the time of the separation is low, whereas the AD removal treatment of the aqueous phase is low advantageous in the case where the temperature at the time of the separation is high.

From the results of Examples 16 to 21, it is evident that under the constant AD concentration and MA concentration conditions, at a higher temperature at the time of the separation, the AD distribution coefficient is smaller, and even in a system where methyl acetate is present, at a higher temperature, the rate of distribution of AD to the organic phase tends to be relatively higher. Specifically, from the viewpoint of acetaldehyde removal efficiency, the AD removal treatment of the organic phase is highly advantageous in the case where the temperature at the time of the separation is high, whereas the AD removal treatment of the organic phase is low advantageous in the case where the temperature at the time of the separation is low. On the other hand, even in a system where methyl acetate is present, the AD removal treatment of the aqueous phase is highly advantageous in the case where the temperature at the time of the separation is low, whereas the AD removal treatment of the aqueous phase is low advantageous in the case where the temperature at the time of the separation is high. From another viewpoint, in the case of using a step or equipment for the AD removal treatment of the organic phase, it is preferred to set the liquid temperature at the time of the separation in the separation step to a high temperature, regardless of the presence or absence of methyl acetate. Also, in the case of using a step or equipment for the AD removal treatment of the aqueous phase, it is preferred to set the liquid temperature at the time of the separation in the separation step to a low temperature.

From the results of Examples 22 to 26, 4, and 17, it is evident that as the charging mixture has a higher MA concentration and the aqueous phase and the organic phase have higher MA concentrations, the AD distribution coefficient is smaller so that the rate of distribution of AD to the organic phase tends to be relatively higher. Specifically, from the viewpoint of acetaldehyde removal efficiency, the AD removal treatment of the organic phase is highly advantageous in the case where the MA concentrations in the aqueous phase and the organic phase are high, whereas the AD removal treatment of the organic phase is low advantageous in the case where the MA concentrations in the aqueous phase and the organic phase are low. On the other hand, the AD removal treatment of the aqueous phase is highly advantageous in the case where the MA concentrations in the aqueous phase and the organic phase are low, whereas the AD removal treatment of the aqueous phase is low advantageous in the case where the MA concentrations in the aqueous phase and the organic phase are high. From another viewpoint, in the case of using a step or equipment for the AD removal treatment of the organic phase, it is preferred to increase the MA concentration in the aqueous phase and/or the organic phase in the separation step by adjusting, for example, reaction conditions for a reaction vessel, evaporation conditions for an evaporator, and distillation conditions for a vapor stream obtained in the evaporation step. Also, in the case of using a step or equipment for the AD removal treatment of the aqueous phase, it is preferred to decrease the MA concentrations in the aqueous phase and the organic phase in the separation step by adjusting, for example, reaction conditions for a reaction vessel, evaporation conditions for an evaporator, and distillation conditions for a vapor stream obtained in the evaporation step. From the results of Examples 22 to 26, it is evident that as the charging mixture has a higher MA concentration and the aqueous phase and/or the organic phase have higher MA concentrations, not only the AD distribution coefficient but the MA distribution coefficient is smaller.

From the results of Reference Examples 1 and 2, it is evident that the AD distribution coefficient is not much changed by the AC concentrations of the charging mixture, the aqueous phase, and the organic phase. Specifically, from the viewpoint of acetaldehyde removal efficiency, the AC concentration is not much significant for comparing the advantages of the method of the AD removal treatment of the organic phase and the method of the AD removal treatment of the aqueous phase.

The configurations according to the present invention and variations or modifications thereof will be listed below as a summary of the above description.

Appendix 1: A method for producing acetic acid, comprising:

a carbonylation reaction step of reacting methanol with carbon monoxide in the presence of a catalyst system comprising a metal catalyst and methyl iodide, acetic acid, methyl acetate, and water in a reaction vessel to produce acetic acid;

an evaporation step of separating the reaction mixture obtained in the carbonylation reaction step into a vapor stream and a residual liquid stream in an evaporator;

a lower boiling point component removal step of separating the vapor stream by distillation into an overhead stream rich in at least one lower boiling point component selected from methyl iodide and acetaldehyde and an acetic acid stream rich in acetic acid;

a separation step of separating a process stream containing at least water, acetic acid, methyl iodide, and acetaldehyde into an aqueous phase and an organic phase; and an acetaldehyde separation and removal step for separating and removing the acetaldehyde derived from the process stream, wherein the separation step satisfies at least one of the following conditions (i) to (v), and at least a portion of the organic phase is treated in the acetaldehyde separation and removal step:

(i) an acetaldehyde concentration in the aqueous phase is not less than 0.045% by mass, and/or an acetaldehyde concentration in the organic phase is not less than 0.013% by mass;

(ii) a temperature at the time of the separation is not less than −5° C. (e.g., −5° C. to 90° C.)

(iii) a methyl acetate concentration in the aqueous phase is not less than 1.2% by mass, and/or a methyl acetate concentration in the organic phase is not less than 2.2% by mass, and/or the sum of the methyl acetate concentration in the aqueous phase and the methyl acetate concentration in the organic phase is not less than 3.4% by mass;

(iv) an acetaldehyde distribution coefficient [{acetaldehyde concentration (% by mass) of the aqueous phase}/{acetaldehyde concentration (% by mass) of the organic phase}] is not more than 4.1 (e.g., 0.5 to 4.1); and (v) a methyl acetate distribution coefficient [{methyl acetate concentration (% by mass) of the aqueous phase}/{methyl acetate concentration (% by mass) of the organic phase}] is not more than 0.53 (e.g., 0.15 to 0.53).

Appendix 2: The method for producing acetic acid according to Appendix 1, wherein the catalyst system further comprises an ionic iodide.

Appendix 3: The method for producing acetic acid according to appendix 1 or 2, wherein in the condition (i), the acetaldehyde concentration in the aqueous phase is not less than 0.045% by mass, and the acetaldehyde concentration in the organic phase is not less than 0.013% by mass.

Appendix 4: The method for producing acetic acid according to any one of appendixes 1 to 3, wherein in the condition (i), the acetaldehyde concentration in the aqueous phase is 0.045 to 35% by mass (preferably 0.15 to 10% by mass, further preferably 0.2 to 2.0% by mass).

Appendix 5: The method for producing acetic acid according to any one of appendixes 1 to 4, wherein in the condition (i), the acetaldehyde concentration in the organic phase is 0.013 to 30% by mass (preferably 0.05 to 5.0% by mass, further preferably 0.1 to 1.0% by mass).

Appendix 6: The method for producing acetic acid according to any one of appendixes 1 to 5, wherein in the case of satisfying the condition (i), an acetaldehyde concentration in a liquid to be subjected to the separation is not less than 0.026% by mass (e.g., 0.026 to 32% by mass, preferably 0.10 to 8.0% by mass, further preferably 0.15 to 1.8% by mass).

Appendix 7: The method for producing acetic acid according to any one of appendixes 1 to 6, wherein in the condition (ii), the temperature at the time of the separation is not less than 0° C. (e.g., 0 to 90° C., further preferably not less than 10° C. (e.g., 10 to 90° C.), particularly preferably a temperature of higher than 70° C. (e.g., more than 70° C. and not more than 90° C.)

Appendix 8: The method for producing acetic acid according to any one of appendixes 1 to 7, wherein in the condition (iii), the methyl acetate concentration in the aqueous phase is not less than 1.2% by mass, and the methyl acetate concentration in the organic phase is not less than 2.2% by mass.

Appendix 9: The method for producing acetic acid according to any one of appendixes 1 to 8, wherein in the condition (iii), the methyl acetate concentration in the aqueous phase is 1.2 to 15% by mass (preferably 2.5 to 12% by mass, further preferably 6.0 to 11% by mass).

Appendix 10: The method for producing acetic acid according to any one of appendixes 1 to 9, wherein in the condition (iii), the methyl acetate concentration in the organic phase is 2.2 to 60% by mass (preferably 5.8 to 48% by mass, further preferably 19 to 42% by mass).

Appendix 11: The method for producing acetic acid according to any one of Appendix 1 to 10, wherein in the condition (iii), the sum of the methyl acetate concentration in the aqueous phase and the methyl acetate concentration in the organic phase is 3.4 to 75% by mass (preferably 8.3 to 60% by mass (e.g., 10 to 40% by mass), further preferably 25 to 53% by mass).

Appendix 12: The method for producing acetic acid according to any one of appendixes 1 to 11, wherein in the case of satisfying the condition (iii), a methyl acetate concentration in the liquid to be subjected to the separation is 2.0 to 50% by mass (preferably 5.0 to 38% by mass, further preferably 15 to 31% by mass).

Appendix 13 The method for producing acetic acid according to any one of appendixes 1 to 12, wherein in the condition (iv), the acetaldehyde distribution coefficient is not more than 3.35 (e.g., 0.6 to 3.35, more preferably less than 1.5 (e.g., not less than 0.7 and less than 1.5), further preferably less than 1.1 (e.g., not less than 0.8 and less than 1.1)).

Appendix 14: The method for producing acetic acid according to appendix 13, wherein the acetaldehyde distribution coefficient is set to less than 1.1 by not less than 1 method selected from the group consisting of setting the acetaldehyde concentration in the aqueous phase to more than 28.1% by mass, setting the acetaldehyde concentration in the organic phase to more than 24.8% by mass, setting the acetaldehyde concentration in the liquid to be subjected to the separation to more than 26.0% by mass, setting the temperature at the time of the separation to more than 70° C., setting the methyl acetate concentration in the aqueous phase to more than 12.0% by mass, setting the methyl acetate concentration in the organic phase to more than 47.6% by mass, and setting the methyl acetate concentration in the liquid to be subjected to the separation to more than 38.2% by mass.

Appendix 15: The method for producing acetic acid according to any one of appendixes 1 to 14, wherein in the condition (v), the methyl acetate distribution coefficient is not more than 0.44 (e.g., 0.20 to 0.44, further preferably less than 0.25 (e.g., not less than 0.20 and less than 0.25)).

Appendix 16: The method for producing acetic acid according to any one of appendixes 1 to 15, wherein the separation step satisfies at least the conditions (i), (ii), and (iii) at the same time.

Appendix 17: The method for producing acetic acid according to any one of appendixes 1 to 16, wherein the separation step satisfies at least the conditions (i), (ii), (iii), and (iv) at the same time.

Appendix 18: The method for producing acetic acid according to any one of appendixes 1 to 17, wherein the separation step satisfies all of the conditions (i), (ii), (iii), (iv), and (v).

Appendix 19: A method for producing acetic acid by reacting methanol with carbon monoxide in the presence of a catalyst system comprising a metal catalyst and methyl iodide, acetic acid, methyl acetate, and water, comprising:

a separation step of separating a process stream containing at least water, acetic acid, methyl iodide, and acetaldehyde into an aqueous phase and an organic phase; and an acetaldehyde separation and removal step for separating and removing the acetaldehyde derived from the process stream, wherein the separation step satisfies at least one of the following conditions (i) to (v), and at least a portion of the organic phase is treated in the acetaldehyde separation and removal step:

(i) an acetaldehyde concentration in the aqueous phase is not less than 0.045% by mass, and/or an acetaldehyde concentration in the organic phase is not less than 0.013% by mass;

(ii) a temperature at the time of the separation is not less than −5° C. (e.g., −5° C. to 90° C.)

(iii) a methyl acetate concentration in the aqueous phase is not less than 1.2% by mass, and/or a methyl acetate concentration in the organic phase is not less than 2.2% by mass, and/or the sum of the methyl acetate concentration in the aqueous phase and the methyl acetate concentration in the organic phase is not less than 3.4% by mass;

(iv) an acetaldehyde distribution coefficient [{acetaldehyde concentration (% by mass) of the aqueous phase}/{acetaldehyde concentration (% by mass) of the organic phase}] is not more than 4.1 (e.g., 0.5 to 4.1); and (v) a methyl acetate distribution coefficient [{methyl acetate concentration (% by mass) of the aqueous phase}/{methyl acetate concentration (% by mass) of the organic phase}] is not more than 0.53 (e.g., 0.15 to 0.53).

Appendix 20: The method for producing acetic acid according to appendix 19, wherein the catalyst system further comprises an ionic iodide.

Appendix 21: The method for producing acetic acid according to appendix 19 or 20, wherein in the condition (i), the acetaldehyde concentration in the aqueous phase is not less than 0.045% by mass, and the acetaldehyde concentration in the organic phase is not less than 0.013% by mass.

Appendix 22: The method for producing acetic acid according to any one of appendixes 19 to 21, wherein in the condition (i), the acetaldehyde concentration in the aqueous phase is 0.045 to 35% by mass (preferably 0.15 to 10% by mass, further preferably 0.2 to 2.0% by mass).

Appendix 23: The method for producing acetic acid according to any one of appendixes 19 to 22, wherein in the condition (i), the acetaldehyde concentration in the organic phase is 0.013 to 30% by mass (preferably 0.05 to 5.0% by mass, further preferably 0.1 to 1.0% by mass).

Appendix 24: The method for producing acetic acid according to any one of appendixes 19 to 23, wherein in the case of satisfying the condition (i), an acetaldehyde concentration in a liquid to be subjected to the separation is not less than 0.026% by mass (e.g., 0.026 to 32% by mass, preferably 0.10 to 8.0% by mass, further preferably 0.15 to 1.8% by mass).

Appendix 25: The method for producing acetic acid according to any one of appendixes 19 to 24, wherein in the condition (ii), the temperature at the time of the separation is not less than 0° C. (e.g., 0 to 90° C., further preferably not less than 10° C. (e.g., 10 to 90° C.), particularly preferably a temperature of higher than 70° C. (e.g., more than 70° C. and not more than 90° C.)

Appendix 26: The method for producing acetic acid according to any one of appendixes 19 to 25, wherein in the condition (iii), the methyl acetate concentration in the aqueous phase is not less than 1.2% by mass, and the methyl acetate concentration in the organic phase is not less than 2.2% by mass.

Appendix 27: The method for producing acetic acid according to any one of appendixes 19 to 26, wherein in the condition (iii), the methyl acetate concentration in the aqueous phase is 1.2 to 15% by mass (preferably 2.5 to 12% by mass, further preferably 6.0 to 11% by mass).

Appendix 28: The method for producing acetic acid according to any one of appendixes 19 to 27, wherein in the condition (iii), the methyl acetate concentration in the organic phase is 2.2 to 60% by mass (preferably 5.8 to 48% by mass, further preferably 19 to 42% by mass).

Appendix 29: The method for producing acetic acid according to any one of appendixes 19 to 28, wherein in the condition (iii), the sum of the methyl acetate concentration in the aqueous phase and the methyl acetate concentration in the organic phase is 3.4 to 75% by mass (preferably 8.3 to 60% by mass (e.g., 10 to 40% by mass), further preferably 25 to 53% by mass).

Appendix 30: The method for producing acetic acid according to any one of appendixes 19 to 29, wherein in the case of satisfying the condition (iii), the methyl acetate concentration in the liquid to be subjected to the separation is 2.0 to 50% by mass (preferably 5.0 to 38% by mass, further preferably 15 to 31% by mass).

Appendix 31: The method for producing acetic acid according to any one of appendixes 19 to 30, wherein in the condition (iv), the acetaldehyde distribution coefficient is not more than 3.35 (e.g., 0.6 to 3.35, more preferably less than 1.5 (e.g., not less than 0.7 and less than 1.5), further preferably less than 1.1 (e.g., not less than 0.8 and less than 1.1)).

Appendix 32: The method for producing acetic acid according to appendix 31, wherein the acetaldehyde distribution coefficient is set to less than 1.1 by not less than 1 method selected from the group consisting of setting the acetaldehyde concentration in the aqueous phase to more than 28.1% by mass, setting the acetaldehyde concentration in the organic phase to more than 24.8% by mass, setting the acetaldehyde concentration in the liquid to be subjected to the separation to more than 26.0% by mass, setting the temperature at the time of the separation to more than 70° C., setting the methyl acetate concentration in the aqueous phase to more than 12.0% by mass, setting the methyl acetate concentration in the organic phase to more than 47.6% by mass, and setting the methyl acetate concentration in the liquid to be subjected to the separation to more than 38.2% by mass.

Appendix 33: The method for producing acetic acid according to any one of appendixes 19 to 32, wherein in the condition (v), the methyl acetate distribution coefficient is not more than 0.44 (e.g., 0.20 to 0.44, further preferably less than 0.25 (e.g., not less than 0.20 and less than 0.25)).

Appendix 34: The method for producing acetic acid according to any one of appendixes 19 to 33, wherein the separation step satisfies at least the conditions (i), (ii), and (iii) at the same time.

Appendix 35: The method for producing acetic acid according to any one of appendixes 19 to 34, wherein the separation step satisfies at least the conditions (i), (ii), (iii), and (iv) at the same time.

Appendix 36: The method for producing acetic acid according to any one of appendixes 19 to 35, wherein the separation step satisfies all of the conditions (i), (ii), (iii), (iv), and (v).

Appendix 37: A method for producing acetic acid, comprising:
a carbonylation reaction step of reacting methanol with carbon monoxide in the presence of a catalyst system comprising a metal catalyst and methyl iodide, acetic acid, methyl acetate, and water in a reaction vessel to produce acetic acid;
an evaporation step of separating the reaction mixture obtained in the carbonylation reaction step into a vapor stream and a residual liquid stream in an evaporator;
a lower boiling point component removal step of separating the vapor stream by distillation into an overhead stream rich in at least one lower boiling point component selected from methyl iodide and acetaldehyde and an acetic acid stream rich in acetic acid;
a separation step of separating a process stream containing at least water, acetic acid, methyl iodide, and acetaldehyde into an aqueous phase and an organic phase; and
an acetaldehyde separation and removal step for separating and removing the acetaldehyde derived from the process stream, wherein
the separation step satisfies at least one of the following conditions (vi) to (x), and at least a portion of the aqueous phase is treated in the acetaldehyde separation and removal step:
(vi) an acetaldehyde concentration in the aqueous phase is not more than 28.1% by mass, and/or an acetaldehyde concentration in the organic phase is not more than 24.8% by mass;
(vii) a temperature at the time of the separation is not more than 70° C.;
(viii) a methyl acetate concentration in the aqueous phase is not more than 12.0% by mass, and/or a methyl acetate concentration in the organic phase is not more than 47.6% by mass, and/or the sum of the methyl acetate concentration in the aqueous phase and the methyl acetate concentration in the organic phase is not more than 59.6% by mass;
(ix) an acetaldehyde distribution coefficient [{acetaldehyde concentration (% by mass) of the aqueous phase}/{acetaldehyde concentration (% by mass) of the organic phase}] is not less than 1.1; and
(x) a methyl acetate distribution coefficient [{methyl acetate concentration (% by mass) of the aqueous phase}/{methyl acetate concentration (% by mass) of the organic phase}] is not less than 0.25 (e.g., 0.25 to 0.70).

Appendix 38: The method for producing acetic acid according to appendix 37, wherein the catalyst system further comprises an ionic iodide.

Appendix 39: The method for producing acetic acid according to appendix 37 or 38, wherein in the condition (vi), the acetaldehyde concentration in the aqueous phase is not more than 28.1% by mass, and the acetaldehyde concentration in the organic phase is not more than 24.8% by mass.

Appendix 40: The method for producing acetic acid according to any one of appendixes 37 to 39, wherein in the condition (vi), the acetaldehyde concentration in the aqueous phase is 0.045 to 28.1% by mass (preferably 0.098 to 10% by mass, further preferably 0.098 to 3.0% by mass, particularly preferably 0.098 to 1.0% by mass (e.g., 0.15 to 0.9% by mass)).

Appendix 41: The method for producing acetic acid according to any one of appendixes 37 to 40, wherein in the condition (vi), the acetaldehyde concentration in the organic phase is 0.013 to 24.8% by mass (preferably 0.030 to 2.0% by mass, further preferably 0.030 to 0.50% by mass, particularly preferably 0.030 to 0.24% by mass).

Appendix 42: The method for producing acetic acid according to any one of appendixes 37 to 41, wherein in the case of satisfying the condition (vi), an acetaldehyde concentration in a liquid to be subjected to the separation is not more than 26.0% by mass (e.g., 0.026 to 26.0% by mass, preferably 0.057 to 10% by mass, further preferably 0.057 to 3.0% by mass, particularly preferably 0.057 to 1.0% by mass (e.g., 0.057 to 0.42% by mass)).

Appendix 43: The method for producing acetic acid according to any one of appendixes 37 to 42, wherein in the condition (vii), the temperature at the time of the separation is −5° C. to 70° C. (preferably −5° C. to 51° C., further preferably −5° C. to 41° C. (e.g., −5° C. to 31° C.)).

Appendix 44: The method for producing acetic acid according to any one of appendixes 37 to 43, wherein in the condition (viii), the methyl acetate concentration in the aqueous phase is not more than 12.0% by mass, and the methyl acetate concentration in the organic phase is not more than 47.6% by mass.

Appendix 45: The method for producing acetic acid according to any one of appendixes 37 to 44, wherein in the condition (viii), the methyl acetate concentration in the aqueous phase is 1.2 to 12.0% by mass (preferably 2.0 to 12.0% by mass, further preferably 5.0 to 12.0% by mass (e.g., 6.0 to 12.0% by mass)).

Appendix 46: The method for producing acetic acid according to any one of appendixes 37 to 45, wherein in the condition (viii), the methyl acetate concentration in the organic phase is 2.2 to 47.6% by mass (preferably 5.0 to 42% by mass, further preferably 8.0 to 35% by mass (e.g., 10 to 30% by mass)).

Appendix 47: The method for producing acetic acid according to any one of appendixes 37 to 46, wherein in the condition (viii), the sum of the methyl acetate concentration in the aqueous phase and the methyl acetate concentration in the organic phase is 4.2 to 59.6% by mass (preferably 10 to 54% by mass, further preferably 14 to 47% by mass (e.g., 16 to 42% by mass)).

Appendix 48: The method for producing acetic acid according to any one of appendixes 37 to 47, wherein in the case of satisfying the condition (viii), a methyl acetate concentration in the liquid to be subjected to the separation is not more than 38.2% by mass (e.g., 2.0 to 38.2% by mass, preferably 5.0 to 31% by mass, further preferably 10 to 25% by mass).

Appendix 49: The method for producing acetic acid according to any one of appendixes 37 to 48, wherein in the condition (ix), the acetaldehyde distribution coefficient is 1.1 to 8.0 (preferably 1.5 to 6.0, further preferably 1.9 to 5.0).

Appendix 50: The method for producing acetic acid according to any one of appendixes 37 to 49, wherein in the condition (x), the methyl acetate distribution coefficient is not less than 0.26 (e.g., 0.26 to 0.65, preferably not less than 0.28 (e.g., 0.28 to 0.60)).

Appendix 51: The method for producing acetic acid according to any one of appendixes 37 to 50, wherein the separation step satisfies at least the conditions (vi), (vii), and (viii) at the same time.

Appendix 52: The method for producing acetic acid according to any one of appendix 37 to 51, wherein the separation step satisfies at least the conditions (vi), (vii), (viii), and (ix) at the same time.

Appendix 53: The method for producing acetic acid according to any one of appendixes 37 to 52, wherein the separation step satisfies all of the conditions (vi), (vii), (viii), (ix), and (x).

Appendix 54: A method for producing acetic acid by reacting methanol with carbon monoxide in the presence of a catalyst system comprising a metal catalyst and methyl iodide, acetic acid, methyl acetate, and water, comprising a separation step of separating a process stream containing at least water, acetic acid, methyl iodide, and acetaldehyde into an aqueous phase and an organic phase; and an acetaldehyde separation and removal step for separating and removing the acetaldehyde derived from the process stream, wherein the separation step satisfies at least one of the following conditions (vi) to (x), and at least a portion of the aqueous phase is treated in the acetaldehyde separation and removal step:

(vi) an acetaldehyde concentration in the aqueous phase is not more than 28.1% by mass, and/or an acetaldehyde concentration in the organic phase is not more than 24.8% by mass;

(vii) a temperature at the time of the separation is not more than 70° C.;

(viii) a methyl acetate concentration in the aqueous phase is not more than 12.0% by mass, and/or a methyl acetate concentration in the organic phase is not more than 47.6% by mass, and/or the sum of the methyl acetate concentration in the aqueous phase and the methyl acetate concentration in the organic phase is not more than 59.6% by mass;

(ix) an acetaldehyde distribution coefficient [{acetaldehyde concentration (% by mass) of the aqueous phase}/{acetaldehyde concentration (% by mass) of the organic phase}] is not less than 1.1; and (x) a methyl acetate distribution coefficient [{methyl acetate concentration (% by mass) of the aqueous phase}/{methyl acetate concentration (% by mass) of the organic phase}] is not less than 0.25 (e.g., 0.25 to 0.70).

Appendix 55: The method for producing acetic acid according to appendix 54, wherein the catalyst system further comprises an ionic iodide.

Appendix 56: The method for producing acetic acid according to appendix 54 or 55, wherein in the condition (vi), the acetaldehyde concentration in the aqueous phase is not more than 28.1% by mass, and the acetaldehyde concentration in the organic phase is not more than 24.8% by mass.

Appendix 57: The method for producing acetic acid according to any one of appendixes 54 to 56, wherein in the condition (vi), the acetaldehyde concentration in the aqueous phase is 0.045 to 28.1% by mass (preferably 0.098 to 10% by mass, further preferably 0.098 to 3.0% by mass, particularly preferably 0.098 to 1.0% by mass (e.g., 0.15 to 0.9% by mass)).

Appendix 58: The method for producing acetic acid according to any one of appendixes 54 to 57, wherein in the condition (vi), the acetaldehyde concentration in the organic phase is 0.013 to 24.8% by mass (preferably 0.030 to 2.0% by mass, further preferably 0.030 to 0.50% by mass, particularly preferably 0.030 to 0.24% by mass).

Appendix 59: The method for producing acetic acid according to any one of appendixes 54 to 58, wherein in the case of satisfying the condition (vi), an acetaldehyde concentration in a liquid to be subjected to the separation is not more than 26.0% by mass (e.g., 0.026 to 26.0% by mass, preferably 0.057 to 10% by mass, further preferably 0.057 to 3.0% by mass, particularly preferably 0.057 to 1.0% by mass (e.g., 0.057 to 0.42% by mass)).

Appendix 60: The method for producing acetic acid according to any one of appendixes 54 to 59, wherein in the condition (vii), the temperature at the time of the separation is −5° C. to 70° C. (preferably −5° C. to 51° C., further preferably −5° C. to 41° C. (e.g., −5° C. to 31° C.)).

Appendix 61: The method for producing acetic acid according to any one of appendixes 54 to 60, wherein in the condition (viii), the methyl acetate concentration in the aqueous phase is not more than 12.0% by mass, and the methyl acetate concentration in the organic phase is not more than 47.6% by mass.

Appendix 62: The method for producing acetic acid according to any one of appendixes 54 to 61, wherein in the condition (viii), the methyl acetate concentration in the aqueous phase is 1.2 to 12.0% by mass (preferably 2.0 to 12.0% by mass, further preferably 5.0 to 12.0% by mass (e.g., 6.0 to 12.0% by mass)).

Appendix 63: The method for producing acetic acid according to any one of appendixes 54 to 62, wherein in the condition (viii), the methyl acetate concentration in the organic phase is 2.2 to 47.6% by mass (preferably 5.0 to 42% by mass, further preferably 8.0 to 35% by mass (e.g., 10 to 30% by mass)).

Appendix 64: The method for producing acetic acid according to any one of appendixes 54 to 63, wherein in the condition (viii), the sum of the methyl acetate concentration in the aqueous phase and the methyl acetate concentration in the organic phase is 4.2 to 59.6% by mass (preferably 10 to 54% by mass, further preferably 14 to 47% by mass (e.g., 16 to 42% by mass)).

Appendix 65: The method for producing acetic acid according to any one of appendixes 54 to 64, wherein in the case of satisfying the condition (viii), a methyl acetate concentration in the liquid to be subjected to the separation is not more than 38.2% by mass (e.g., 2.0 to 38.2% by mass, preferably 5.0 to 31% by mass, further preferably 10 to 25% by mass).

Appendix 66: The method for producing acetic acid according to any one of appendixes 54 to 65, wherein in the condition (ix), the acetaldehyde distribution coefficient is 1.1 to 8.0 (preferably 1.5 to 6.0, further preferably 1.9 to 5.0).

Appendix 67: The method for producing acetic acid according to any one of appendixes 54 to 66, wherein in the condition (x), the methyl acetate distribution coefficient is not less than 0.26 (e.g., 0.26 to 0.65, preferably not less than 0.28 (e.g., 0.28 to 0.60)).

Appendix 68: The method for producing acetic acid according to any one of appendixes 54 to 67, wherein the separation step satisfies at least the conditions (vi), (vii), and (viii) at the same time.

Appendix 69: The method for producing acetic acid according to any one of appendixes 54 to 68, wherein the separation step satisfies at least the conditions (vi), (vii), (viii), and (ix) at the same time.

Appendix 70: The method for producing acetic acid according to any one of appendixes 54 to 69, wherein the separation step satisfies all of the conditions (vi), (vii), (viii), (ix), and (x).

Appendix 71: The method for producing acetic acid according to any one of appendixes 1 to 70, further comprising a scrubber step of separating offgas from the process into a stream rich in carbon monoxide and a stream rich in acetic acid by absorption treatment with an absorption solvent containing at least acetic acid.

INDUSTRIAL APPLICABILITY

The method for producing acetic acid of the present invention can be used as industrial method for producing acetic acid by carbonylation process of a methanol method (acetic acid process of a methanol method).

REFERENCE SIGNS LIST

1: reaction vessel
2: evaporator
3, 5, and 6: distillation column
4: decanter
7: ion exchange resin column
8: scrubber system
9: acetaldehyde separation and removal system
16: reaction mixture feed line
17: vapor stream discharge line
18 and 19: residual liquid stream recycle line
54: carbon monoxide-containing gas introduction line
55 and 56: potassium hydroxide introduction line
57: catalyst circulating pump
91: distillation column (first acetaldehyde removal column)
92: extraction column
93: distillation column (second acetaldehyde removal column)
94: distillation column (extractive distillation column)
95: decanter
96: decanter
97: distillation column (acetaldehyde removal column)
98: distillation column (extractive distillation column)
99: decanter
200: chimney tray
300: liquid-liquid equilibrium measurement apparatus

The invention claimed is:
1. A method for producing acetic acid by reacting methanol with carbon monoxide in the presence of a catalyst system comprising a metal catalyst and methyl iodide, acetic acid, methyl acetate, and water, the method comprising:
    separating a process stream containing at least water, acetic acid, methyl iodide, and acetaldehyde into an aqueous phase and an organic phase, wherein an acetaldehyde concentration in a liquid to be subjected to the separation is not less than 0.026% by mass and a methyl acetate concentration in the liquid to be subjected to the separation step is 2.0 to 50% by mass, wherein
    the following condition (i), the following condition (ii), the following condition (iii), and at least one of the following conditions (iv) and (v) are satisfied:
    (i) an acetaldehyde concentration in the aqueous phase is not less than 0.045% by mass, and/or an acetaldehyde concentration in the organic phase is not less than 0.013% by mass;
    (ii) a temperature at the time of the separation is not less than −5° C.;
    (iii) a methyl acetate concentration in the organic phase is 5.8% to 60% by mass;
    (iv) an acetaldehyde distribution coefficient [{acetaldehyde concentration (% by mass) of the aqueous phase}/{acetaldehyde concentration (% by mass) of the organic phase}] is not more than 4.1; and
    (v) a methyl acetate distribution coefficient [{methyl acetate concentration (% by mass) of the aqueous phase}/{methyl acetate concentration (% by mass) of the organic phase}] is not more than 0.53; and
    separating and removing the acetaldehyde derived from the process stream, wherein at least a portion of the organic phase is treated.

2. The method for producing acetic acid according to claim 1, wherein the catalyst system further comprises an ionic iodide.

3. The method for producing acetic acid according to claim 1, wherein all of the conditions (i), (ii), (iii), (iv), and (v) are satisfied.

4. A method for producing acetic acid, comprising:
carbonylating methanol with carbon monoxide in the presence of a catalyst system comprising a metal catalyst and methyl iodide, acetic acid, methyl acetate, and water in a reaction vessel to produce acetic acid;
evaporating a reaction mixture obtained by the carbonylation to separate into a vapor stream and a residual liquid stream in an evaporator;
removing a lower boiling point component by distillation to separate the vapor stream into an overhead stream rich in at least one lower boiling point component selected from methyl iodide and acetaldehyde and an acetic acid stream rich in acetic acid;
separating a process stream containing at least water, acetic acid, methyl iodide, and acetaldehyde into an aqueous phase and an organic phase, wherein an acetaldehyde concentration in a liquid to be subjected to the separation is not more than 26.0% by mass and a methyl acetate concentration in the liquid to be subjected to the separation step is not more than 38.2% by mass, wherein
the following condition (vi), the following condition (vii), the following condition (viii), and at least one of the following conditions (ix) and (x) are satisfied:
(vi) an acetaldehyde concentration in the aqueous phase is not more than 28.1% by mass, and/or an acetaldehyde concentration in the organic phase is not more than 24.8% by mass;
(vii) a temperature at the time of the separation is not more than 70° C.;
(viii) a methyl acetate concentration in the aqueous phase is 5.0% to 12.0% by mass, and/or a methyl acetate concentration in the organic phase is 8.0% to 47.6% by mass, and/or the sum of the methyl acetate concentration in the aqueous phase and the methyl acetate concentration in the organic phase is 15% to 59.6% by mass;
(ix) an acetaldehyde distribution coefficient [{acetaldehyde concentration (% by mass) of the aqueous phase}/{acetaldehyde concentration (% by mass) of the organic phase}] is 1.1 to 4.5; and
(x) a methyl acetate distribution coefficient [{methyl acetate concentration (% by mass) of the aqueous phase}/{methyl acetate concentration (% by mass) of the organic phase}] is 0.25 to 0.53; and
separating and removing the acetaldehyde derived from the process stream, wherein at least a portion of the aqueous phase is treated.

5. The method for producing acetic acid according to claim 4, wherein the catalyst system further comprises an ionic iodide.

6. The method for producing acetic acid according to claim 4, wherein all of the conditions (vi), (vii), (viii), (ix), and (x) are satisfied.

7. A method for producing acetic acid by reacting methanol with carbon monoxide in the presence of a catalyst system comprising a metal catalyst and methyl iodide, acetic acid, methyl acetate, and water, the method comprising
separating a process stream containing at least water, acetic acid, methyl iodide, and acetaldehyde into an aqueous phase and an organic phase, wherein an acetaldehyde concentration in a liquid to be subjected to the separation is not more than 26.0% by mass and a methyl acetate concentration in the liquid to be subjected to the separation step is not more than 38.2% by mass, wherein
the following condition (vi), the following condition (vii), the following condition (viii), and at least one of the following conditions (ix) and (x) are satisfied:
(vi) an acetaldehyde concentration in the aqueous phase is not more than 28.1% by mass, and/or an acetaldehyde concentration in the organic phase is not more than 24.8% by mass;
(vii) a temperature at the time of the separation is not more than 70° C.;
(viii) a methyl acetate concentration in the aqueous phase is 5.0% to 12.0% by mass, and/or a methyl acetate concentration in the organic phase is 8.0% to 47.6% by mass, and/or the sum of the methyl acetate concentration in the aqueous phase and the methyl acetate concentration in the organic phase is 14% to 59.6% by mass;
(ix) an acetaldehyde distribution coefficient [{acetaldehyde concentration (% by mass) of the aqueous phase}/{acetaldehyde concentration (% by mass) of the organic phase}] is 1.1 to 4.5; and
(x) a methyl acetate distribution coefficient [{methyl acetate concentration (% by mass) of the aqueous phase}/{methyl acetate concentration (% by mass) of the organic phase}] is 0.25 to 0.53; and
separating and removing the acetaldehyde derived from the process stream, wherein at least a portion of the aqueous phase is treated.

8. The method for producing acetic acid according to claim 7, wherein the catalyst system further comprises an ionic iodide.

9. The method for producing acetic acid according to claim 7, wherein all of the conditions (vi), (vii), (viii), (ix), and (x) are satisfied.

10. The method for producing acetic acid according to claim 1, further comprising separating offgas from the process into a stream rich in carbon monoxide and a stream rich in acetic acid by absorption treatment with an absorption solvent containing at least acetic acid.

11. The method for producing acetic acid according to claim 1, wherein in the condition (iv), the acetaldehyde distribution coefficient is 0.6 to 3.35.

12. The method for producing acetic acid according to claim 1, wherein in the condition (v), the methyl acetate distribution coefficient is 0.20 to 0.44.

13. The method for producing acetic acid according to claim 4, wherein the acetaldehyde concentration in the liquid to be subjected to the separation is 0.057 to 10% by mass.

14. The method for producing acetic acid according to claim 4, wherein the methyl acetate concentration in the liquid to be subjected to the separation is 5.0 to 31% by mass.

15. The method for producing acetic acid according to claim 7, wherein in the condition (vi), the acetaldehyde concentration in the aqueous phase is 0.098 to 10% by mass.

16. The method for producing acetic acid according to claim 7, wherein in the condition (vi), the acetaldehyde concentration in the organic phase is 0.030 to 2.0% by mass.

17. The method for producing acetic acid according to claim 7, wherein in the condition (viii), the methyl acetate concentration in the aqueous phase is 6.0 to 12.0% by mass.

18. The method for producing acetic acid according to claim 7, wherein in the condition (viii), the methyl acetate concentration in the organic phase is 10 to 30% by mass.

19. The method for producing acetic acid according to claim 7, wherein in the condition (viii), the sum of the methyl acetate concentration in the aqueous phase and the methyl acetate concentration in the organic phase is 16 to 42% by mass.

20. The method for producing acetic acid according to claim 7, wherein the methyl acetate concentration in the liquid to be subjected to the separation is 5.0 to 31% by mass.

* * * * *